(12) United States Patent
Green et al.

(10) Patent No.: US 8,933,094 B2
(45) Date of Patent: Jan. 13, 2015

(54) ETHYNYL COMPOUNDS USEFUL FOR TREATMENT OF CNS DISORDER

(71) Applicant: Hoffmann-La Roche Inc., Nutley, NJ (US)

(72) Inventors: Luke Green, Basel (CH); Wolfgang Guba, Muelheim (DE); Georg Jaeschke, Basel (CH); Synese Jolidon, Blauen (CH); Lothar Lindemann, Basel (CH); Heinz Stadler, Basel (CH); Eric Vieira, Frankendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/055,047

(22) Filed: Oct. 16, 2013

(65) Prior Publication Data

US 2014/0073638 A1  Mar. 13, 2014

Related U.S. Application Data

(62) Division of application No. 12/964,785, filed on Dec. 10, 2010, now Pat. No. 8,586,581.

(30) Foreign Application Priority Data

Dec. 17, 2009  (EP) .................................. 09179719

(51) Int. Cl.
*A61K 31/44* (2006.01)
*C07D 513/02* (2006.01)
*C07D 515/02* (2006.01)
*C07D 487/04* (2006.01)
*C07D 471/04* (2006.01)

(52) U.S. Cl.
CPC ............ *C07D 487/04* (2013.01); *C07D 471/04* (2013.01)
USPC ........... 514/300; 514/303; 546/117; 546/119; 546/121

(58) Field of Classification Search
USPC ................... 514/300, 303; 546/117, 119, 121
See application file for complete search history.

(56) References Cited

U.S. PATENT DOCUMENTS

| 2003/0166633 | A1* | 9/2003 | Gaster et al. ............. 514/211.15 |
| 2004/0152738 | A1* | 8/2004 | Gaster et al. .................. 514/341 |
| 2004/0266842 | A1* | 12/2004 | Gaster et al. .................. 514/365 |
| 2005/0014938 | A1* | 1/2005 | Gaster et al. .................... 544/60 |
| 2012/0178742 | A1* | 7/2012 | Henrich et al. .......... 514/217.06 |

FOREIGN PATENT DOCUMENTS

| WO | 02/40476 | 5/2002 |
| WO | 03/042211 | 5/2003 |
| WO | 2011/015343 | 2/2011 |

OTHER PUBLICATIONS

The English translation of the Chinese Office Action, issued on Feb. 27, 2014, in the corresponding Chinese application No. 201080057081.9.
The English translation of the Japanese Office Action, issued on Dec. 10, 2013, in the corresponding Japanese application No. 2012-543676.

* cited by examiner

*Primary Examiner* — Niloofar Rahmani

(57) ABSTRACT

The present invention relates to ethynyl compounds of formula

I wherein X, Y, Z, and $R^4$ are as defined herein
or to a pharmaceutically acceptable salt or acid addition salt, to a racemic mixture, or to its corresponding enantiomer and/or optical isomer and/or stereoisomer thereof. Compounds of formula I are positive allosteric modulators (PAM) of the metabotropic glutamate receptor subtype 5 (mGluR5) and they are therefore useful for the treatment of diseases related to this receptor.

3 Claims, No Drawings

ETHYNYL COMPOUNDS USEFUL FOR TREATMENT OF CNS DISORDER

PRIORITY TO RELATED APPLICATION(S)

This application is a divisional application of U.S. application Ser. No. 12/964,785, filed Dec. 10, 2010, now pending, which claims the benefit of European Patent Application No. 09179719.1, filed Dec. 17, 2009, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:
mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, Tuberous sclerosis as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12(12), 1845-1852 doi:10.1517/13543776.12.12.1845).

A new avenue for developing selective modulators is to identify compounds which act through allosteric mechanism, modulating the receptor by binding to a site different from the highly conserved orthosteric binding site. Positive allosteric modulators of mGluR5 have emerged recently as novel pharmaceutical entities offering this attractive alternative. Positive allosteric modulators have been described, for example in WO2008/151184, WO2006/048771, WO2006/129199 and WO2005/044797 and in *Molecular Pharmacology* (1991), 40, 333-336; *The Journal of Pharmacology and Experimental Therapeutics* (2005) 313(1), 199-206;

Positive allosteric modulators are compounds that do not directly activate receptors by themselves, but markedly potentiate agonist-stimulated responses, increase potency and maximum of efficacy. The binding of these compounds increases the affinity of a glutamate-site agonist at its extracellular N-terminal binding site. Positive allosteric modulation is thus an attractive mechanism for enhancing appropriate physiological receptor activation. There is a scarcity of selective positive allosteric modulators for the mGluR5 receptor. Conventional mGluR5 receptor modulators typically lack satisfactory aqueous solubility and exhibit poor oral bioavailability. Therefore, there remains a need for compounds that overcome these deficiencies and that effectively provide selective positive allosteric modulators for the mGluR5 receptor.

SUMMARY OF THE INVENTION

The present invention provides ethynyl compounds of formula I

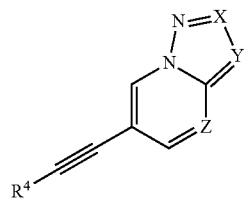

wherein
X is N or C—R$^1$;
Y is N or C—R$^2$;
Z is CH or N;
R$^4$ is a 6-membered aromatic substituent containing 0, 1 or 2 nitrogen atoms, optionally substituted by 1 to 3 groups, selected from halogen, lower alkyl, lower alkoxy and NRR';
R$^1$ is hydrogen, lower alkyl, lower alkoxy, hydroxy, lower hydroxyalkyl, lower cycloalkyl or heterocycloalkyl optionally substituted with hydroxy or alkoxy;
R$^2$ is hydrogen, CN, lower alkyl or heterocycloalkyl;
R and R' are each independently hydrogen or lower alkyl;
or a pharmaceutically acceptable salt or acid addition salt, a racemic mixture, corresponding enantiomer and/or optical isomer, and/or stereoisomer thereof.

Compounds of formula I are distinguished by having valuable therapeutic properties. They are positive allosteric modulators (PAM) of the metabotropic glutamate receptor subtype 5 (mGluR5). They can be used in the treatment or prevention of disorders, relating to positive allosteric modulators for the mGluR5 receptor. The most preferred indications for compounds which are positive allosteric modulators are schizophrenia and cognition.

The present invention relates to compounds of formula I and to their pharmaceutically acceptable salts and pharmaceutical compositions containing them. The invention also provides processes for their production as well as to their use in the treatment or prevention of disorders, relating to positive allosteric modulators for the mGluR5 receptor, such as schizophrenia and cognition and to pharmaceutical compositions containing the compounds of formula I.

DETAILED DESCRIPTION OF THE INVENTION

The following definitions of the general terms used in the present description apply irrespective of whether the terms in question appear alone or in combination.

As used herein, the term "halogen" denotes chlorine, bromine, iodine, and fluorine.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, isopropyl and tert-butyl.

The term "alkoxy" denotes a group —O—R' wherein R' is lower alkyl as defined above.

The term "ethynyl" denotes the group —C≡C—.

The term "lower hydroxyalkyl" denotes a lower alkyl groups as defined above, wherein at least one hydrogen atom is replaced by hydroxy.

The term "lower cycloalkyl" denotes a saturated carbon ring, containing from 3 to 7 carbon ring atoms, for example cyclopropyl, cyclobutyl, cyclopentyl, cyclohexyl or cycloheptyl.

The term "heterocycloalkyl" denotes a saturated carbon ring, containing one or more oxygen or nitrogen atoms, a preferred heteroatom is O. Examples for such rings are tetrahydropyran-2, 3 or 4-yl, pyrrolidinyl, imidazolidinyl, pyrazolidinyl, piperidinyl, piperazinyl or morpholinyl.

The term "6-membered aromatic substituent containing 0, 1 or 2 nitrogen atoms" includes, but not limited to, the following aromatic rings: phenyl, 2,3- or 4-pyridinyl or pyrimidinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In one embodiment, the invention provides compounds of formula I, wherein X is C—$R^1$ and Y is C—$R^2$ and Z is N,

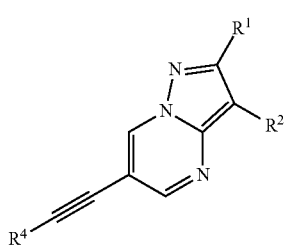

IA wherein
$R^4$ is a 6-membered aromatic substituent containing 0, 1 or 2 nitrogen atoms, optionally substituted by 1 to 3 groups, selected from halogen, lower alkyl, lower alkoxy and NRR';
$R^1$ is hydrogen, lower alkyl, lower alkoxy, hydroxy, lower hydroxyalkyl, lower cycloalkyl or is heterocycloalkyl optionally substituted with hydroxy or alkoxy;

$R^2$ is hydrogen, CN, lower alkyl or heterocycloalkyl;
R and R' are each independently hydrogen or lower alkyl;
or a pharmaceutically acceptable acid addition salt, a racemic mixture, or its corresponding enantiomer and/or optical isomer and/or stereoisomer thereof.

The following compounds are encompassed by formula IA:
6-Phenylethynyl-pyrazolo[1,5-a]pyrimidine;
2-Methyl-6-phenylethynyl-pyrazolo[1,5-a]pyrimidine;
6-(2-Fluoro-phenylethynyl)-2-methyl-pyrazolo[1,5-a]pyrimidine;
6-(3-Fluoro-phenylethynyl)-2-methyl-pyrazolo[1,5-a]pyrimidine;
6-(4-Fluoro-phenylethynyl)-2-methyl-pyrazolo[1,5-a]pyrimidine;
2-Methyl-6-pyridin-4-ylethynyl-pyrazolo[1,5-a]pyrimidine;
2-Methyl-6-p-tolylethynyl-pyrazolo[1,5-a]pyrimidine;
6-(4-Chloro-phenylethynyl)-2-methyl-pyrazolo[1,5-a]pyrimidine;
2-tert-Butyl-6-phenylethynyl-pyrazolo[1,5-a]pyrimidine;
2-tert-Butyl-6-(2-fluoro-phenylethynyl)-pyrazolo[1,5-a]pyrimidine;
2-tert-Butyl-6-(3-fluoro-phenylethynyl)-pyrazolo[1,5-a]pyrimidine;
2-tert-Butyl-6-(4-fluoro-phenylethynyl)-pyrazolo[1,5-a]pyrimidine;
2-tert-Butyl-6-pyridin-3-ylethynyl-pyrazolo[1,5-a]pyrimidine;
2-tert-Butyl-6-pyridin-4-ylethynyl-pyrazolo[1,5-a]pyrimidine;
2-tert-Butyl-6-(4-methoxy-phenylethynyl)-pyrazolo[1,5-a]pyrimidine;
2-tert-Butyl-6-m-tolylethynyl-pyrazolo[1,5-a]pyrimidine;
2-tert-Butyl-6-(3-methoxy-phenylethynyl)-pyrazolo[1,5-a]pyrimidine;
2-Cyclobutyl-6-phenylethynyl-pyrazolo[1,5-a]pyrimidine;
2-tert-Butyl-6-p-tolylethynyl-pyrazolo[1,5-a]pyrimidine;
2-tert-Butyl-6-(4-chloro-phenylethynyl)-pyrazolo[1,5-a]pyrimidine;
2-tert-Butyl-6-(6-chloro-pyridin-3-ylethynyl)-pyrazolo[1,5-a]pyrimidine;
5-(2-tert-Butyl-pyrazolo[1,5-a]pyrimidin-6-ylethynyl)-pyridin-2-ylamine;
2-tert-Butyl-6-(5-chloro-pyridin-3-ylethynyl)-pyrazolo[1,5-a]pyrimidine;
2-tert-Butyl-6-pyrimidin-5-ylethynyl-pyrazolo[1,5-a]pyrimidine;
2-tert-Butyl-6-(3,4-difluoro-phenylethynyl)-pyrazolo[1,5-a]pyrimidine;
6-Phenylethynyl-2-(tetrahydro-pyran-4-yl)-pyrazolo[1,5-a]pyrimidine;
4-(2-tert-Butyl-pyrazolo[1,5-a]pyrimidin-6-ylethynyl)-phenylamine;
2-(6-Phenylethynyl-pyrazolo[1,5-a]pyrimidin-2-yl)-propan-2-ol;
2-tert-Butyl-6-(5-fluoro-pyridin-3-ylethynyl)-pyrazolo[1,5-a]pyrimidine;
6-Phenylethynyl-pyrazolo[1,5-a]pyrimidine-3-carbonitrile;
3-(2-tert-Butyl-pyrazolo[1,5-a]pyrimidin-6-ylethynyl)-phenylamine;
2-(2-tert-Butyl-pyrazolo[1,5-a]pyrimidin-6-ylethynyl)-phenylamine;
2-tert-Butyl-6-(2,5-difluoro-phenylethynyl)-pyrazolo[1,5-a]pyrimidine; and
2-Isopropyl-6-phenylethynyl-pyrazolo[1,5-a]pyrimidine.

In another embodiment, the invention provides compounds of formula IB, wherein X is C—$R^1$, Y is N and Z is CH,

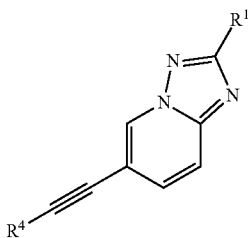

wherein
R⁴ is a 6-membered aromatic substituent containing 0, 1 or 2 nitrogen atoms, optionally substituted by 1 to 3 groups, selected from halogen, lower alkyl, lower alkoxy and NRR';
R¹ is hydrogen, lower alkyl, lower alkoxy, hydroxy, lower hydroxyalkyl, lower cycloalkyl or heterocycloalkyl optionally substituted with hydroxy or alkoxy;
R and R' are each independently hydrogen or lower alkyl;
or a pharmaceutically acceptable acid addition salt, a racemic mixture, or its corresponding enantiomer and/or optical isomer and/or stereoisomer thereof.

The following compounds are encompassed by formula IB:
6-Phenylethynyl-[1,2,4]triazolo[1,5-a]pyridine;
2-tert-Butyl-6-phenylethynyl-[1,2,4]triazolo[1,5-a]pyridine and
2-Methyl-2-(6-phenylethynyl-[1,2,4]triazolo[1,5-a]pyridin-2-yl)-propan-1-ol.

In another embodiment, the invention provides compounds of formula I, wherein X is C—R¹ and Y and Z are N.

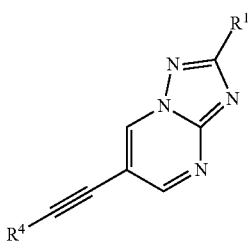

wherein
R⁴ is a 6-membered aromatic substituent containing 0, 1 or 2 nitrogen atoms, optionally substituted by 1 to 3 groups, selected from halogen, lower alkyl, lower alkoxy and NRR';
R¹ is hydrogen, lower alkyl, lower alkoxy, hydroxy, lower hydroxyalkyl, lower cycloalkyl or heterocycloalkyl optionally substituted with hydroxy or alkoxy;
R and R' are each independently hydrogen or lower alkyl;
or a pharmaceutically acceptable acid addition salt, a racemic mixture, or its corresponding enantiomer and/or optical isomer and/or stereoisomer thereof.

The following compounds are encompassed by formula IC:
6-Phenylethynyl-[1,2,4]triazolo[1,5-a]pyrimidine;
2-tert-Butyl-6-phenylethynyl-[1,2,4]triazolo[1,5-a]pyrimidine;
2-tert-Butyl-6-(2,5-difluoro-phenylethynyl)-[1,2,4]triazolo[1,5-a]pyrimidine;
2-tert-Butyl-6-(3-fluoro-phenylethynyl)-[1,2,4]triazolo[1,5-a]pyrimidine;
2-tert-Butyl-6-(3,4-difluoro-phenylethynyl)-[1,2,4]triazolo[1,5-a]pyrimidine;
2-tert-Butyl-6-(5-chloro-pyridin-3-ylethynyl)-[1,2,4]triazolo[1,5-a]pyrimidine;
2-Morpholin-4-yl-6-phenylethynyl-[1,2,4]triazolo[1,5-a]pyrimidine;
2-Morpholin-4-yl-6-m-tolylethynyl-[1,2,4]triazolo[1,5-a]pyrimidine;
6-(3-Fluoro-phenylethynyl)-2-morpholin-4-yl-[1,2,4]triazolo[1,5-a]pyrimidine;
6-(3-Chloro-phenylethynyl)-2-morpholin-4-yl-[1,2,4]triazolo[1,5-a]pyrimidine; and
6-Phenylethynyl-2-pyrrolidin-1-yl-[1,2,4]triazolo[1,5-a]pyrimidine.

A further embodiment, the invention provides compounds of formula I, wherein X is C—R¹, Y is C—R² and Z is CH.

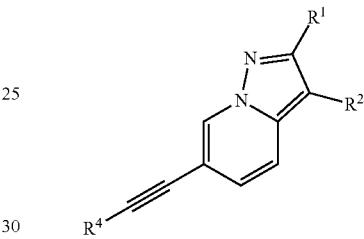

wherein
R⁴ is a 6-membered aromatic substituent containing 0, 1 or 2 nitrogen atoms, optionally substituted by 1 to 3 groups, selected from halogen, lower alkyl, lower alkoxy and NRR';
R¹ is hydrogen, lower alkyl, lower alkoxy, hydroxy, lower hydroxyalkyl, lower cycloalkyl or heterocycloalkyl optionally substituted with hydroxy or alkoxy;
R² is hydrogen, CN, lower alkyl or heterocycloalkyl;
R and R' are each independently hydrogen or lower alkyl;
or a pharmaceutically acceptable acid addition salt, a racemic mixture, or its corresponding enantiomer and/or optical isomer and/or stereoisomer thereof.

The following compounds are encompassed by formula ID:
6-Phenylethynyl-pyrazolo[1,5-a]pyridine and
2-tert-Butyl-6-phenylethynyl-pyrazolo[1,5-a]pyridine.

In a further embodiment, the invention provides compounds of formula I, wherein X is N, Y is C—R² and Z is CH.

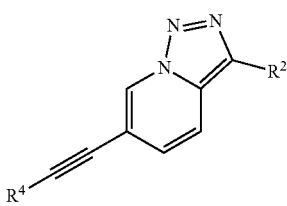

wherein
R⁴ is a 6-membered aromatic substituent containing 0, 1 or 2 nitrogen atoms, optionally substituted by 1 to 3 groups, selected from halogen, lower alkyl, lower alkoxy and NRR';

R² is hydrogen, CN, lower alkyl or heterocycloalkyl;

R and R' are each independently hydrogen or lower alkyl;

or a pharmaceutically acceptable acid addition salt, a racemic mixture, or its corresponding enantiomer and/or optical isomer and/or stereoisomer thereof.

The following compound is encompassed by formula IE:

6-Phenylethynyl-[1,2,3]triazolo[1,5-a]pyridine.

The preparation of compounds of formula I of the present invention can be carried out in sequential or convergent synthetic routes. Syntheses of the compounds of the invention are shown in the following schemes 1 to 6. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variants described below, which process comprises a) reacting a compound of formula 2

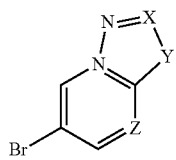

2 with a suitable aryl-acetylene of formula 3

3 to yield a compound of formula I

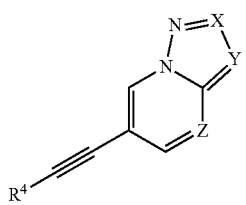

I wherein the substituents are described above, or b) reacting a compound of formula 4

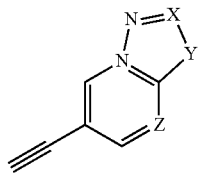

4 with a compound of formula 5

R⁴-hal 5 to yield a compound of formula I

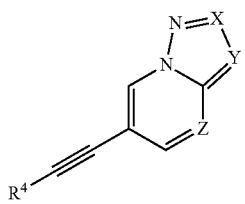

I wherein the substituents are described above and hal is halogen, selected from Cl, Br and I, c) reacting a compound of formula 6

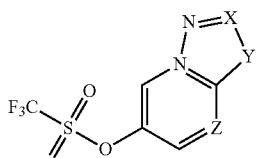

6 with a suitable aryl-acetylene of formula 3

3 to yield a compound of formula I

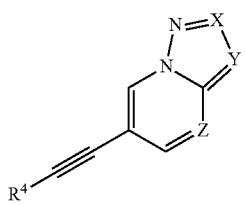

I wherein the substituents are described above, and, if desired, converting the compounds obtained into pharmaceutically acceptable acid addition salts.

The preparation of compounds of formula I is further described in more detail in schemes 1 to 10 and in examples 1-51.

Scheme 1

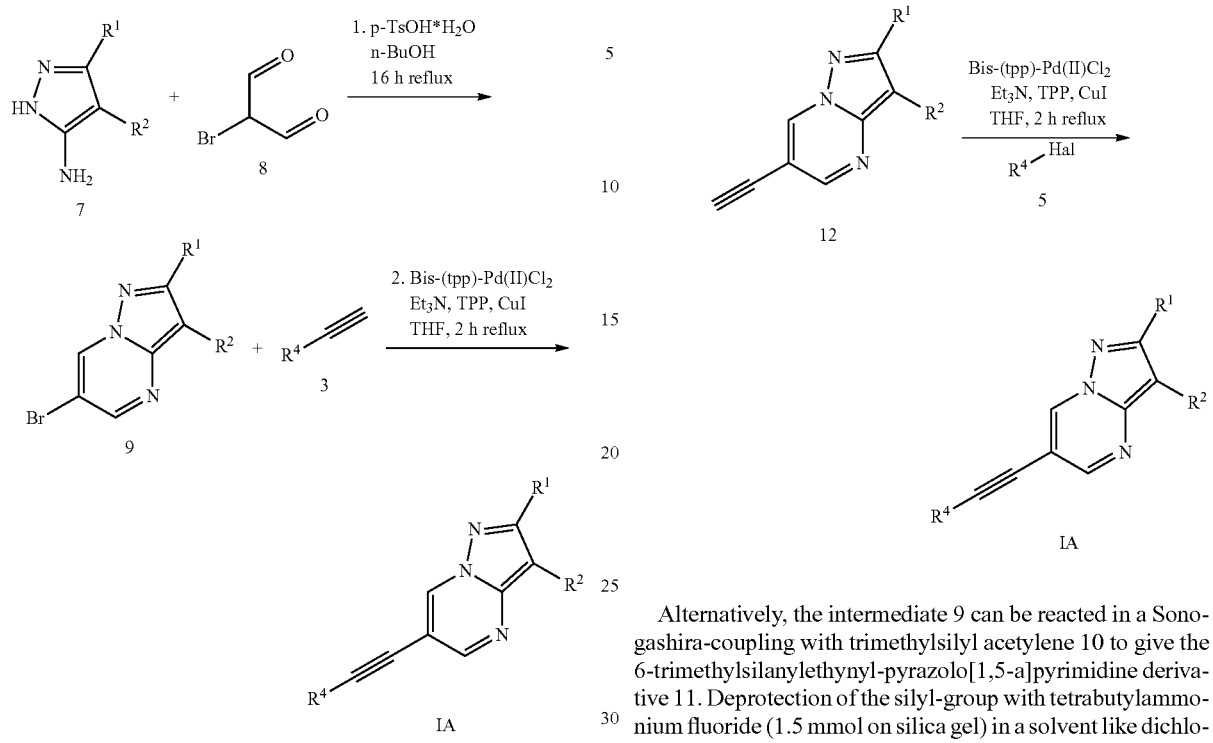

A 6-ethynyl-pyrazolo[1,5-a]pyrimidine of formula IA can be obtained by condensation of an appropriately substituted 2-H-pyrazol-3-ylamine 7 and bromomalonaldehyde 8 with para-toluenesulfonic acid monohydrate in a solvent like n-butanol to yield the corresponding 6-bromo-pyrazolo[1,5-a]pyrimidine derivative 9. Sonogashira coupling of the 6-bromo-pyrazolo[1,5-a]pyrimidine derivative 9 with an appropriately substituted aryl-acetylene 3 yields the desired 6-ethynyl-pyrazolo[1,5-a]pyrimidine of formula IA (scheme 1).

Alternatively, the intermediate 9 can be reacted in a Sonogashira-coupling with trimethylsilyl acetylene 10 to give the 6-trimethylsilanylethynyl-pyrazolo[1,5-a]pyrimidine derivative 11. Deprotection of the silyl-group with tetrabutylammonium fluoride (1.5 mmol on silica gel) in a solvent like dichloromethane yields the corresponding ethynyl derivative 12. Sonogashira coupling of 12 with an appropriately substituted aryl-halogenide yields the desired 6-ethynyl-pyrazolo[1,5-a]pyrimidine of formula IA (scheme 2). This reaction sequence can alternatively be applied by coupling the trimethylsilanyl derivative 11 with an appropriately substituted aryl halogenide under Sonogashira coupling conditions with simultaneous addition of tetrabutylammonium fluoride which realizes the silyl deprotection in-situ.

Scheme 2

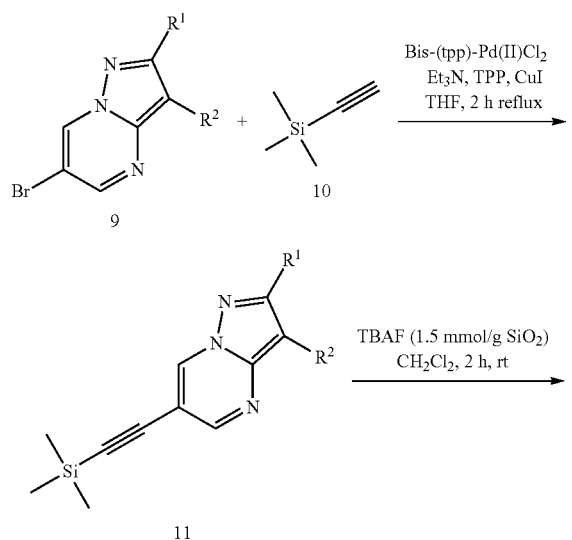

Scheme 3

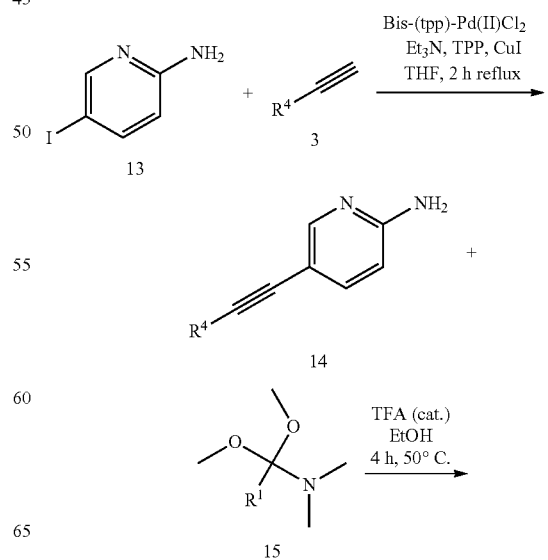

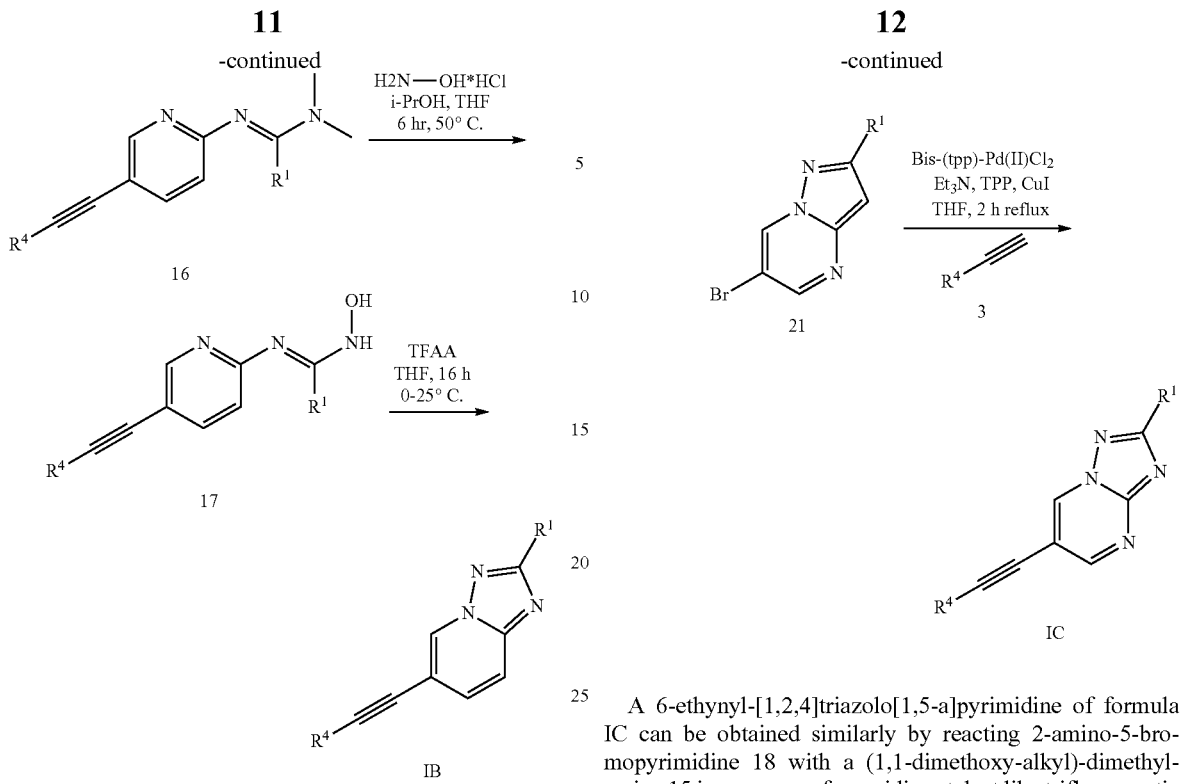

A 6-ethynyl-[1,2,4]triazolo[1,5-a]pyridine of formula IB can be obtained by Sonogashira coupling of an aryl-acetylene 3 with 2-amino-5-iodopyridine 13 to yield the corresponding 5-ethynyl-pyridin-2-ylamine derivative 14. Reaction of 14 with a (1,1-dimethoxy-alkyl)-dimethyl-amine 15 in presence of an acidic catalyst like trifluoroacetic acid and a solvent such as ethanol yields the corresponding amidine 16, which is treated with hydroxylamine hydrochloride in a solvent such as i-PrOH:THF (5:1 v/v) to give the desired N-hydroxyamidine 17. This compound is cyclized with trifluoroacetic anhydride in a solvent such as THF to give the desired 6-ethynyl-[1,2,4]triazolo[1,5-a]pyridine of formula IB (scheme 3).

A 6-ethynyl-[1,2,4]triazolo[1,5-a]pyrimidine of formula IC can be obtained similarly by reacting 2-amino-5-bromopyrimidine 18 with a (1,1-dimethoxy-alkyl)-dimethylamine 15 in presence of an acidic catalyst like trifluoroacetic acid and a solvent such as ethanol to give the corresponding amidine 19, which is treated with hydroxylamine hydrochloride in a solvent such as i-PrOH:THF (5:1 v/v) to give the N-hydroxyamidine 20. This compound is cyclized with trifluoroacetic anhydride in a solvent such as THF to give the desired 6-ethynyl-[1,2,4]triazolo[1,5-a]pyrimidine of formula IC (scheme 4).

Scheme 4

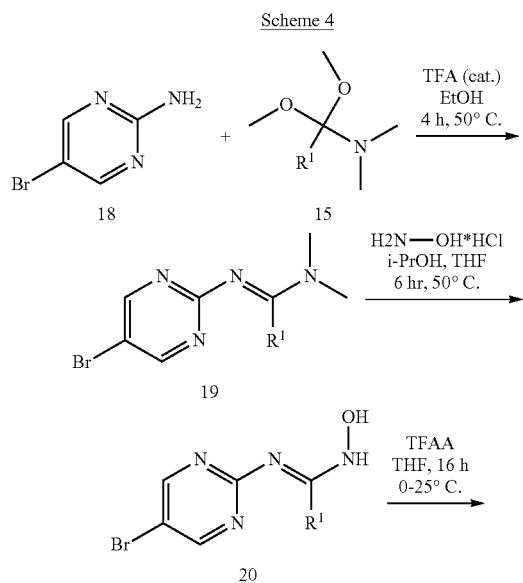

Scheme 5

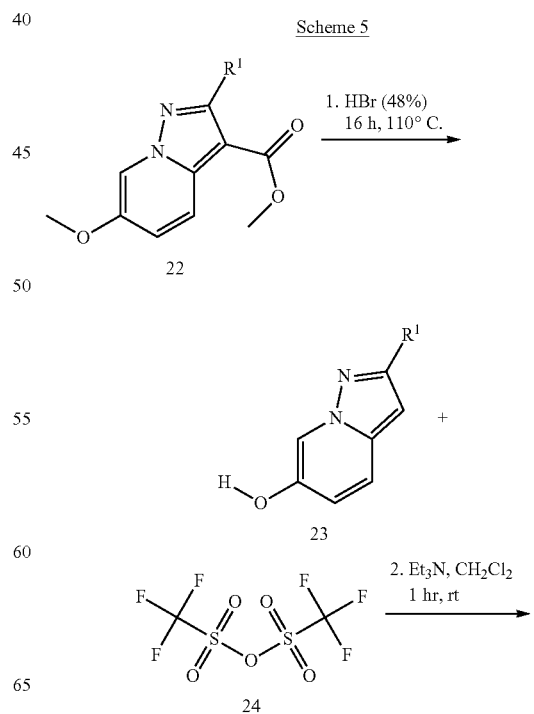

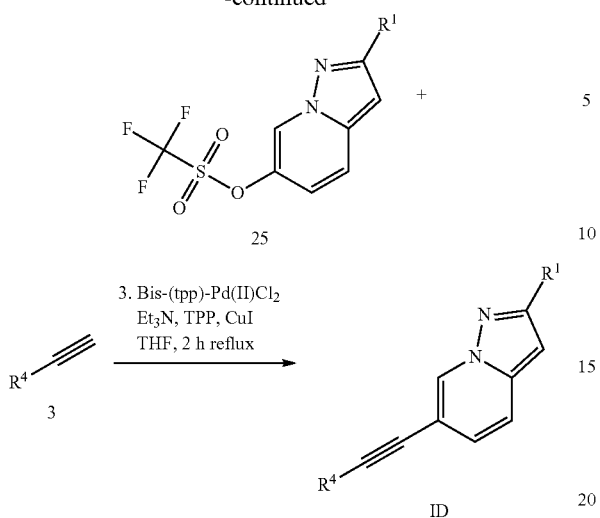

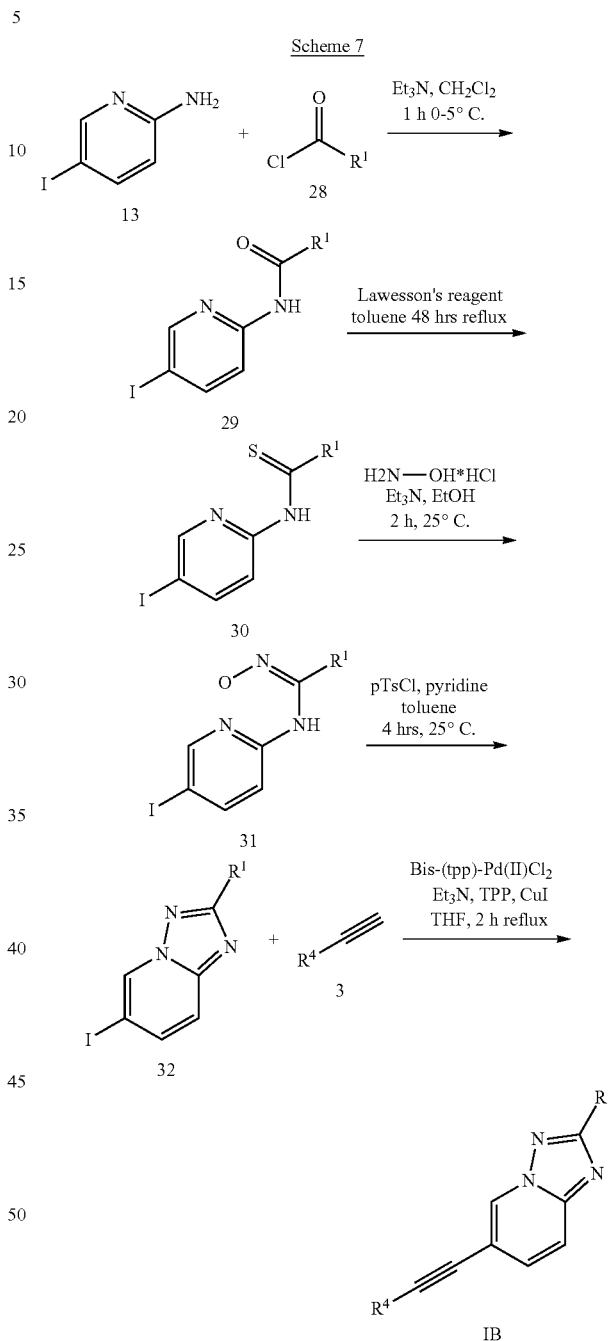

A 6-ethynyl-pyrazolo[1,5-a]pyridine of formula ID can be obtained by decarboxylation of an appropriately substituted 6-methoxy-pyrazolo[1,5-a]pyridine-3-carboxylic acid ester 22 with hydrobromic acid, yielding the corresponding pyrazolo[1,5-a]pyridin-6-ol derivative 23, which is converted to the triflate derivative 25 using trifluoromethanesulfonic anhydride 24 and a base such as triethylamine in a solvent such as dichloromethane. Sonogashira coupling of 25 with an aryl-acetylene of formula 3 yields the desired 6-ethynyl-pyrazolo[1,5-a]pyridine of formula ID (scheme 5).

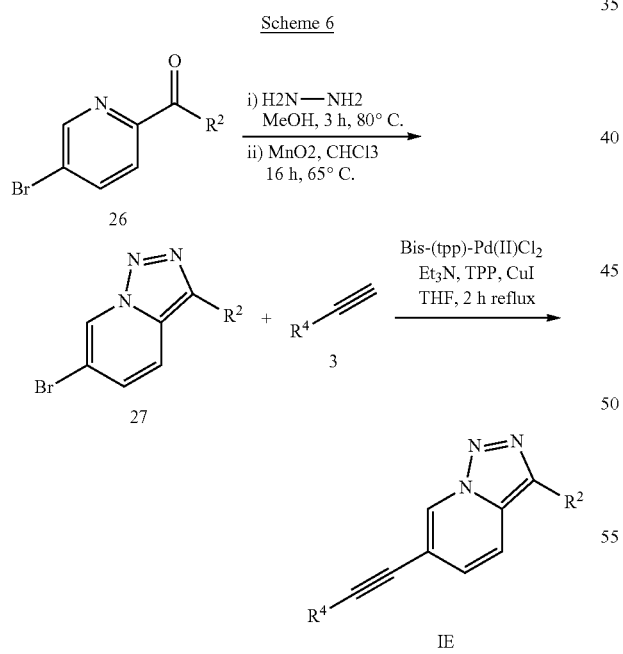

A 6-ethynyl-[1,2,3]triazolo[1,5-a]pyridine of formula IE can be obtained by coupling of an appropriately substituted 5-halopyridine aldehyde or ketone 26 with hydrazine in a solvent such as methanol, followed by oxidation with an oxidizing agent such as manganese dioxide yielding the corresponding 6-bromo-[1,2,3]triazolo[1,5-a]pyridine derivative 27. Sonogashira coupling of 27 with an aryl-acetylene 3 yields the desired 6-ethynyl-[1,2,3]triazolo[1,5-a]pyridine of formula IE (scheme 6).

A 6-ethynyl-[1,2,4]triazolo[1,5-a]pyridine of formula IB can be obtained by reaction of 2-amino-5-iodopyridine 13 with an appropriately substituted acid chloride 28 in the presence of a base such as $Et_3N$ in a solvent like dichloromethane to yield the corresponding N-(5-iodo-pyridin-2-yl)-amide 29. Reaction of 29 with Lawesson's reagent in a solvent like toluene yields the corresponding thioamide 30. Reacting 30 with hydroxylamine hydrochloride and a base such as $Et_3N$ in a solvent like EtOH yields the corresponding hydroxyamidine 31, which is treated with p-TsCl and pyridine in a solvent like toluene to give the desired 6-iodo-[1,2,4]triazolo[1,5-a]

pyridine 32. Sonogashira coupling of 27 with an appropriately substituted aryl-acetylene 3 yields the desired 6-ethynyl-[1,2,4]triazolo[1,5-a]pyridine of formula IB (scheme 7).

dinitro-phenolate 35 from 3-bromopyridine 33 and O-(2,4-dinitro-phenyl)-hydroxylamine 34 in a solvent like acetonitrile. Reacting the pyridinium derivative 35 with an appropriately substituted propynoic acid methyl ester 36 and a base such as $K_2CO_3$ in a solvent like DMF yields the corresponding 6-bromo-pyrazolo[1,5-a]pyridine-3-carboxylic acid ester 37, which is decarboxylated with hydrobromic acid, yielding the corresponding 6-bromo-pyrazolo[1,5-a]pyridine derivative 38. Sonogashira coupling of 38 with an appropriately substituted aryl-acetylene 3 yields the desired 6-ethynyl-pyrazolo[1,5-a]pyridine of formula ID (scheme 8).

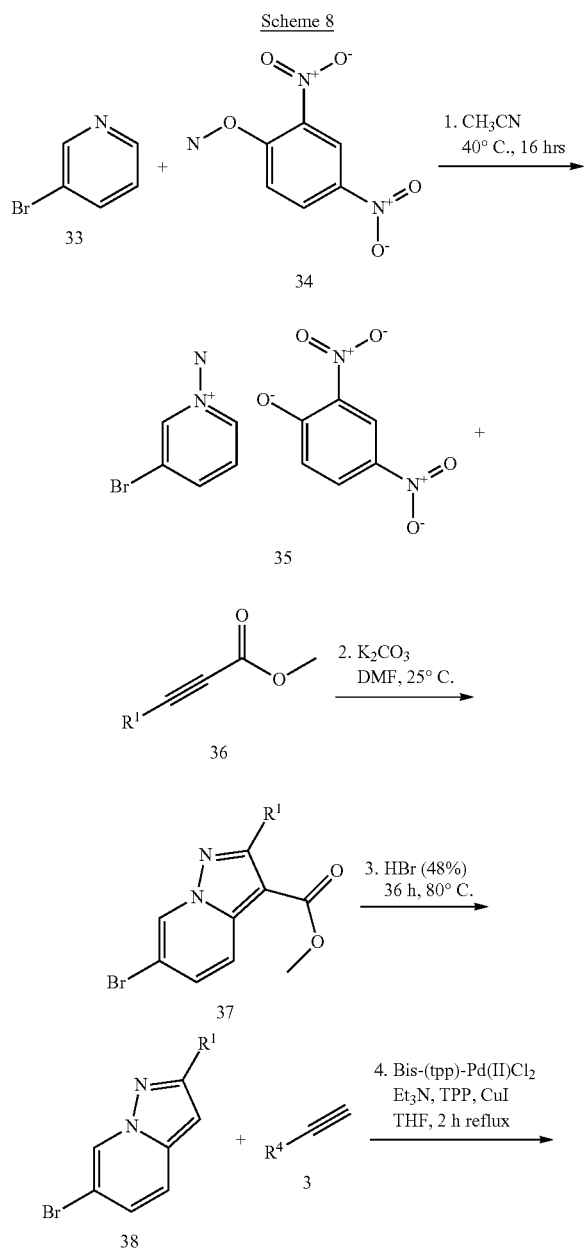

Scheme 8

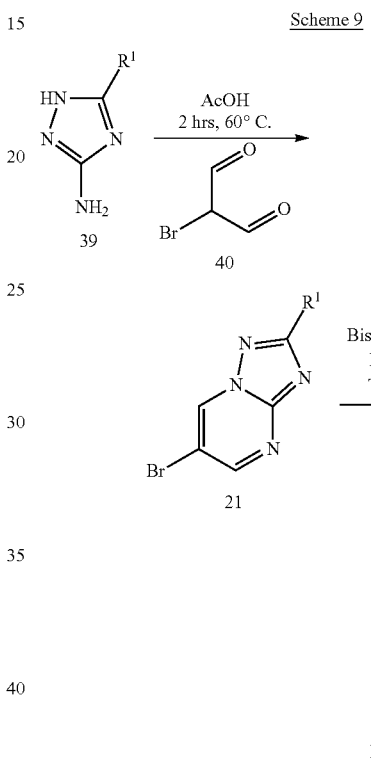

Scheme 9

A 6-ethynyl-[1,2,4]triazolo[1,5-a]pyrimidine of formula IC can be obtained by condensation of an appropriately substituted 1H-1,2,4-triazol-5-amine 39 with 2-bromomalonaldehyde 40 in AcOH to give the corresponding 6-bromo-[1,2,4]triazolo[1,5-a]pyrimidine 21. Sonogashira coupling of 21 with an appropriately substituted aryl-acetylene 3 yields the desired 6-ethynyl-[1,2,4]triazolo[1,5-a]pyrimidine of formula IC (scheme 9).

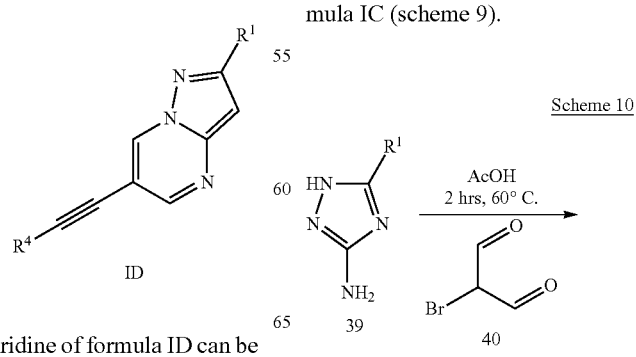

Scheme 10

A 6-ethynyl-pyrazolo[1,5-a]pyridine of formula ID can be obtained by formation of 1-amino-3-bromo-pyridinium 2,4-

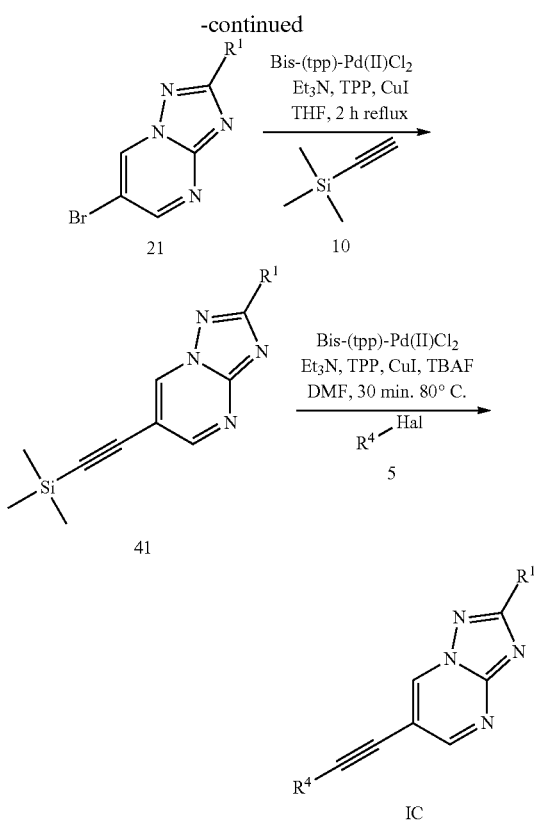

A 6-ethynyl-[1,2,4]triazolo[1,5-a]pyrimidine of formula IC can also be obtained by condensation of an appropriately substituted 1H-1,2,4-triazol-5-amine 39 with 2-bromomalonaldehyde 40 in AcOH to give the corresponding 6-bromo-[1,2,4]triazolo[1,5-a]pyrimidine 21. Sonogashira coupling of 21 with trimethylsilyl acetylene 10 yields the corresponding 6-trimethylsilanylethynyl-[1,2,4]triazolo[1,5-a]pyrimidine 41. Sonogashira coupling with in-situ desilylation of 41 and an appropriately substituted aryl-halogenide 5 yields the desired 6-ethynyl-[1,2,4]triazolo[1,5-a]pyrimidine of formula IC (scheme 10).

Preferably, the compound of formula I as described herein as well as its pharmaceutically acceptable salt is used in the treatment or prevention of psychosis, epilepsy, schizophrenia, Alzheimer's disease, cognitive disorders and memory deficits, chronic and acute pain, restricted brain function caused by bypass operations or transplants, poor blood supply to the brain, spinal cord injuries, head injuries, hypoxia caused by pregnancy, cardiac arrest and hypoglycaemia, ischemia, Huntington's chorea, amyotrophic lateral sclerosis (ALS), dementia caused by AIDS, eye injuries, retinopathy, idiopathic parkinsonism or parkinsonism caused by medicaments, muscle spasms, convulsions, migraine, urinary incontinence, gastrointestinal reflux disorder, liver damage or failure whether drug or disease induced, Fragile-X syndrom, Down syndrom, autism, nicotine addiction, opiate addiction, anxiety, vomiting, dyskinesia, eating disorders, in particular bulimia or anorexia nervosa, and depressions, particularly for the treatment and prevention of acute and/or chronic neurological disorders, anxiety, the treatment of chronic and acute pain, urinary incontinence and obesity.

The preferred indications are schizophrenia and cognitive disorders.

Present invention further relates to the use of a compound of formula I as described herein, as well as its pharmaceutically acceptable salt, for the manufacture of a medicament, preferably for the treatment and prevention of the above-mentioned disorders.

Biological Assay and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to $EC_{20}$ (typically around 80 µM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the list of examples below are shown the corresponding results for compounds which have $EC_{50}<500$ nM.

| Ex. | Structure | Name | EC$_{50}$ (nM) mGlu5PAM | Eff. (%) |
|---|---|---|---|---|
| 1 | 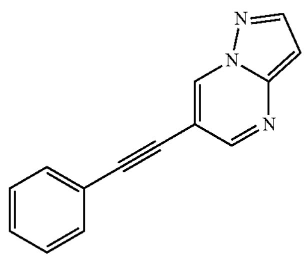 [SMILES: C(#Cc1cnc2ccnn2c1)c1ccccc1] | 6-Phenylethynyl-pyrazolo[1,5-a]pyrimidine | 70 | 116 |
| 2 | 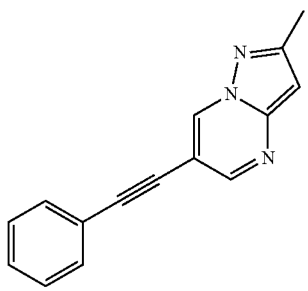 [SMILES: Cc1cc2ncc(C#Cc3ccccc3)cn2n1] | 2-Methyl-6-phenylethynyl-pyrazolo[1,5-a]pyrimidine | 49 | 99 |
| 3 | 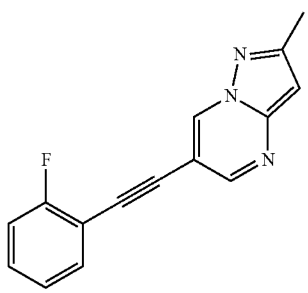 [SMILES: Cc1cc2ncc(C#Cc3ccccc3F)cn2n1] | 6-(2-Fluoro-phenylethynyl)-2-methyl-pyrazolo[1,5-a]pyrimidine | 47 | 81 |
| 4 | 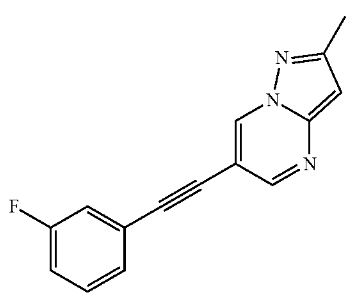 [SMILES: Cc1cc2ncc(C#Cc3cccc(F)c3)cn2n1] | 6-(3-Fluoro-phenylethynyl)-2-methyl-pyrazolo[1,5-a]pyrimidine | 42 | 77 |
| 5 | 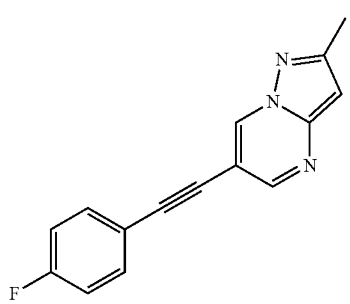 [SMILES: Cc1cc2ncc(C#Cc3ccc(F)cc3)cn2n1] | 6-(4-Fluoro-phenylethynyl)-2-methyl-pyrazolo[1,5-a]pyrimidine | 78 | 74 |

-continued

| Ex. | Structure | Name | EC$_{50}$ (nM) mGlu5PAM | Eff. (%) |
|---|---|---|---|---|
| 6 | 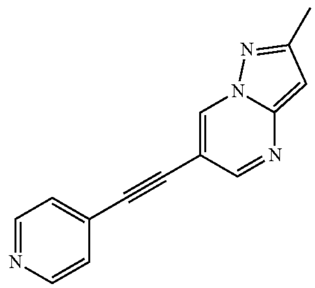 [SMILES: Cc1cc2ncc(C#Cc3ccncc3)cn2n1] | 2-Methyl-6-pyridin-4-ylethynyl-pyrazolo[1,5-a]pyrimidine | 498 | 82 |
| 7 | 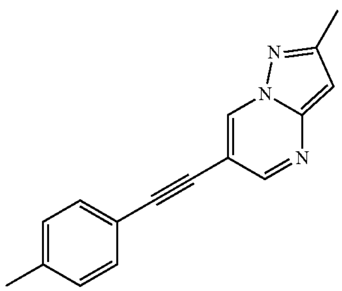 | 2-Methyl-6-p-tolylethynyl-pyrazolo[1,5-a]pyrimidine | 132 | 73 |
| 8 | 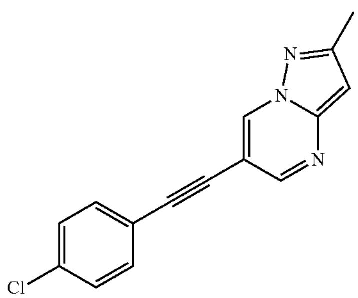 [SMILES: Cc1cc2ncc(C#Cc3ccc(Cl)cc3)cn2n1] | 6-(4-Chloro-phenylethynyl)-2-methyl-pyrazolo[1,5-a]pyrimidine | 148 | 69 |
| 9 | 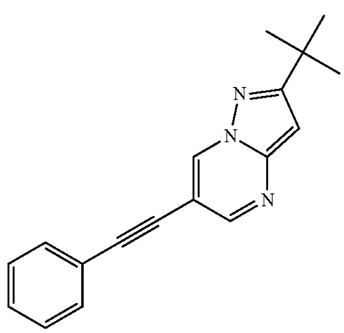 [SMILES: CC(C)(C)c1cc2ncc(C#Cc3ccccc3)cn2n1] | 2-tert-Butyl-6-phenylethynyl-pyrazolo[1,5-a]pyrimidine | 5 | 75 |
| 10 | 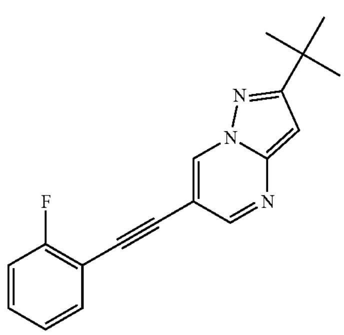 | 2-tert-Butyl-6-(2-fluoro-phenylethynyl)-pyrazolo[1,5-a]pyrimidine | 19 | 80 |

-continued

| Ex. | Structure | Name | EC$_{50}$ (nM) mGlu5PAM | Eff. (%) |
|---|---|---|---|---|
| 11 | 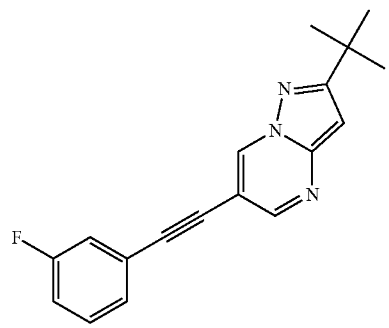 [SMILES: CC(C)(C)c1cc2ncc(C#Cc3cccc(F)c3)cn2n1] | 2-tert-Butyl-6-(3-fluoro-phenylethynyl)-pyrazolo[1,5-a]pyrimidine | 5 | 86 |
| 12 | 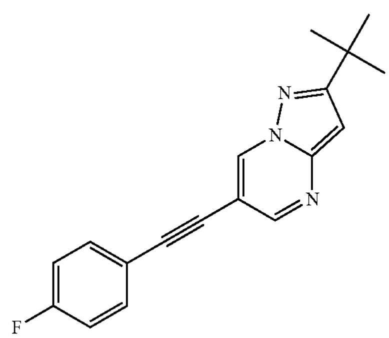 [SMILES: CC(C)(C)c1cc2ncc(C#Cc3ccc(F)cc3)cn2n1] | 2-tert-Butyl-6-(4-fluoro-phenylethynyl)-pyrazolo[1,5-a]pyrimidine | 7 | 75 |
| 13 | 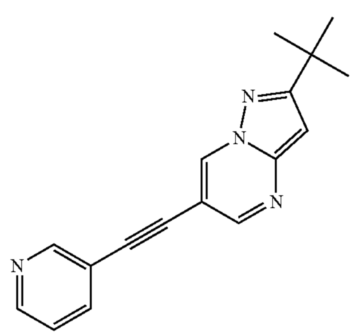 [SMILES: CC(C)(C)c1cc2ncc(C#Cc3cccnc3)cn2n1] | 2-tert-Butyl-6-pyridin-3-ylethynyl-pyrazolo[1,5-a]pyrimidine | 33 | 88 |
| 14 | 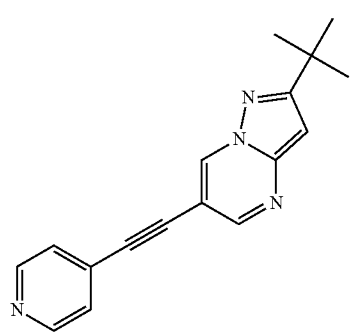 [SMILES: CC(C)(C)c1cc2ncc(C#Cc3ccncc3)cn2n1] | 2-tert-Butyl-6-pyridin-4-ylethynyl-pyrazolo[1,5-a]pyrimidine | 4 | 37 |

-continued
| Ex. | Structure | Name | EC₅₀ (nM) mGlu5PAM | Eff. (%) |
|---|---|---|---|---|
| 15 | 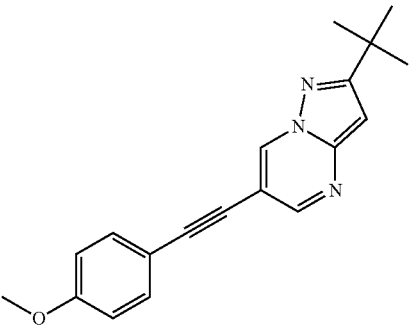 [SMILES: COc1ccc(C#Cc2cnc3cc(C(C)(C)C)nn3c2)cc1] | 2-tert-Butyl-6-(4-methoxy-phenylethynyl)-pyrazolo[1,5-a]pyrimidine | 68 | 53 |
| 16 | 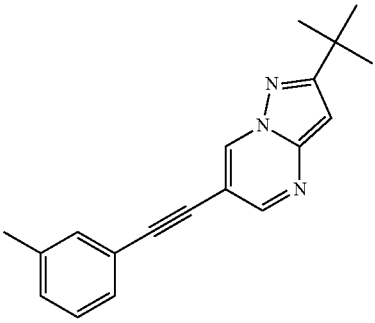 [SMILES: Cc1cccc(C#Cc2cnc3cc(C(C)(C)C)nn3c2)c1] | 2-tert-Butyl-6-m-tolylethynyl-pyrazolo[1,5-a]pyrimidine | 100 | 50 |
| 17 | 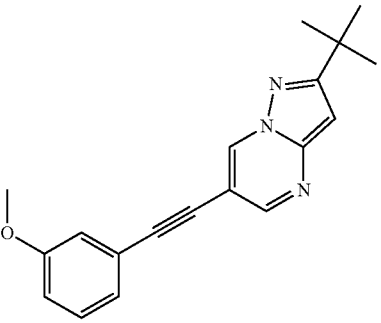 [SMILES: COc1cccc(C#Cc2cnc3cc(C(C)(C)C)nn3c2)c1] | 2-tert-Butyl-6-(3-methoxy-phenylethynyl)-pyrazolo[1,5-a]pyrimidine | 104 | 41 |
| 18 | 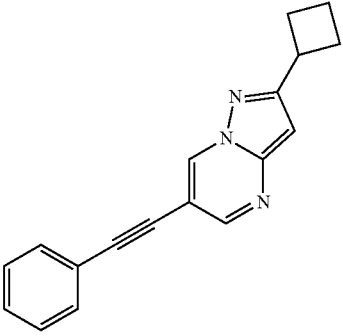 [SMILES: C(#Cc1cnc2cc(C3CCC3)nn2c1)c1ccccc1] | 2-Cyclobutyl-6-phenylethynyl-pyrazolo[1,5-a]pyrimidine | 182 | 102 |

-continued

| Ex. | Structure | Name | EC$_{50}$ (nM) mGlu5PAM | Eff. (%) |
|---|---|---|---|---|
| 19 | 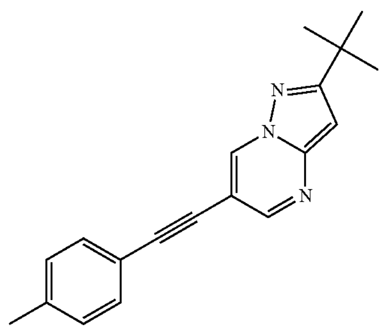 [SMILES: Cc1ccc(C#Cc2cnc3cc(C(C)(C)C)nn3c2)cc1] | 2-tert-Butyl-6-p-tolylethynyl-pyrazolo[1,5-a]pyrimidine | 100 | 68 |
| 20 | 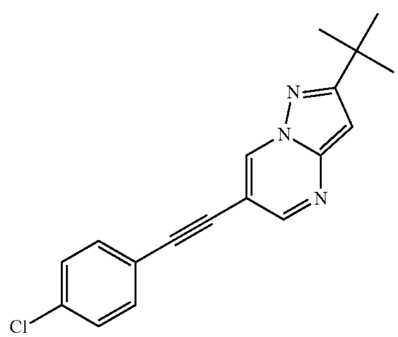 [SMILES: CC(C)(C)c1cc2ncc(C#Cc3ccc(Cl)cc3)cn2n1] | 2-tert-Butyl-6-(4-chloro-phenylethynyl)-pyrazolo[1,5-a]pyrimidine | 400 | 89 |
| 21 | 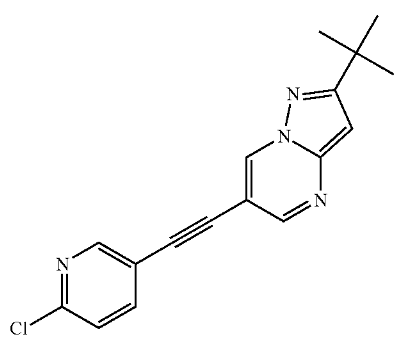 [SMILES: CC(C)(C)c1cc2ncc(C#Cc3ccc(Cl)nc3)cn2n1] | 2-tert-Butyl-6-(6-chloro-pyridin-3-ylethynyl)-pyrazolo[1,5-a]pyrimidine | 183 | 77 |
| 22 | 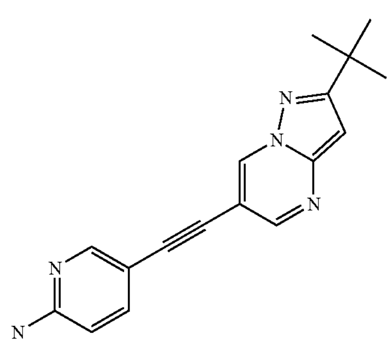 [SMILES: CC(C)(C)c1cc2ncc(C#Cc3ccc(N)nc3)cn2n1] | 5-(2-tert-Butyl-pyrazolo[1,5-a]pyrimidin-6-ylethynyl)-pyridin-2-ylamine | 255 | 98 |

-continued

| Ex. | Structure | Name | EC$_{50}$ (nM) mGlu5PAM | Eff. (%) |
|---|---|---|---|---|
| 23 | 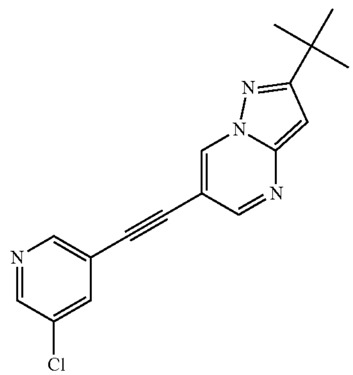 [SMILES: CC(C)(C)c1cc2ncc(C#Cc3cncc(Cl)c3)cn2n1] | 2-tert-Butyl-6-(5-chloro-pyridin-3-ylethynyl)-pyrazolo[1,5-a]pyrimidine | 34 | 59 |
| 24 | 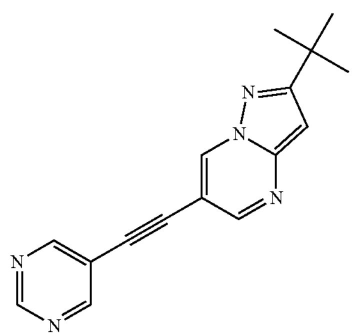 [SMILES: CC(C)(C)c1cc2ncc(C#Cc3cncnc3)cn2n1] | 2-tert-Butyl-6-pyrimidin-5-ylethynyl-pyrazolo[1,5-a]pyrimidine | 181 | 68 |
| 25 | 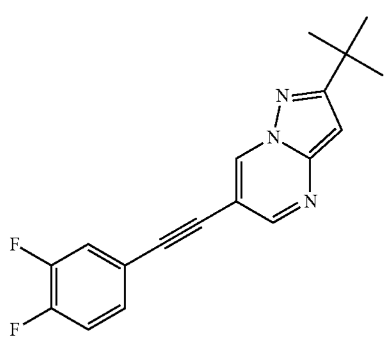 [SMILES: CC(C)(C)c1cc2ncc(C#Cc3ccc(F)c(F)c3)cn2n1] | 2-tert-Butyl-6-(3,4-difluoro-phenylethynyl)-pyrazolo[1,5-a]pyrimidine | 45 | 93 |
| 26 | 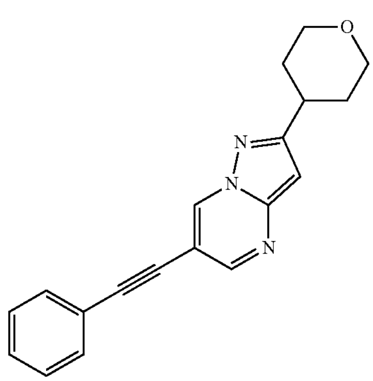 [SMILES: C(#Cc1cnc2cc(C3CCOCC3)nn2c1)c1ccccc1] | 6-Phenylethynyl-2-(tetrahydro-pyran-4-yl)-pyrazolo[1,5-a]pyrimidine | 472 | 124 |

-continued

| Ex. | Structure | Name | EC$_{50}$ (nM) mGlu5PAM | Eff. (%) |
|---|---|---|---|---|
| 27 | 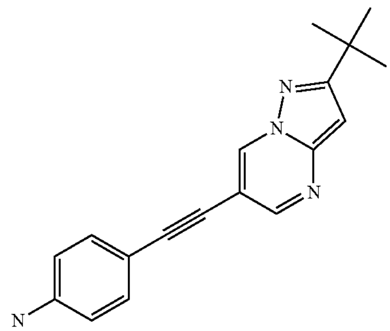 [SMILES: CC(C)(C)c1cc2ncc(C#Cc3ccc(N)cc3)cn2n1] | 4-(2-tert-Butyl-pyrazolo[1,5-a]pyrimidin-6-ylethynyl)-phenylamine | 41 | 99 |
| 28 | 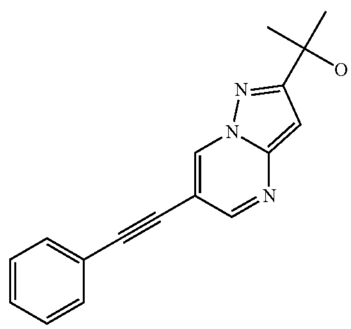 [SMILES: CC(C)(O)c1cc2ncc(C#Cc3ccccc3)cn2n1] | 2-(6-Phenylethynyl-pyrazolo[1,5-a]pyrimidin-2-yl)-propan-2-ol | 152 | 59 |
| 29 | 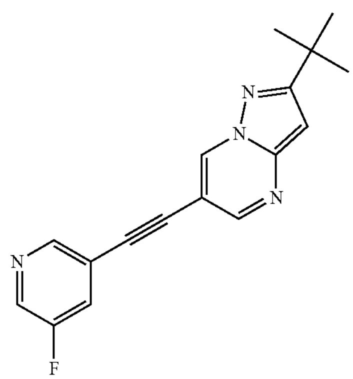 [SMILES: CC(C)(C)c1cc2ncc(C#Cc3cncc(F)c3)cn2n1] | 2-tert-Butyl-6-(5-fluoro-pyridin-3-ylethynyl)-pyrazolo[1,5-a]pyrimidine | 161 | 61 |
| 30 | 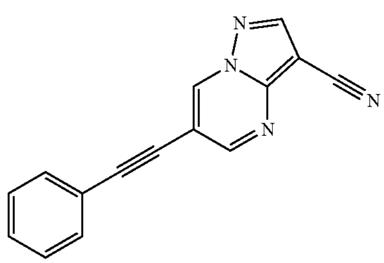 [SMILES: N#Cc1cnn2cc(C#Cc3ccccc3)cnc12] | 6-Phenylethynyl-pyrazolo[1,5-a]pyrimidine-3-carbonitrile | 310 | 63 |
| 31 | 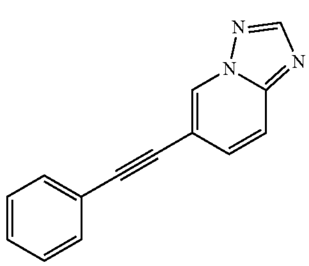 [SMILES: C(#Cc1ccc2ncnn2c1)c1ccccc1] | 6-Phenylethynyl-[1,2,4]triazolo[1,5-a]pyridine | 274 | 123 |

-continued

| Ex. | Structure | Name | EC$_{50}$ (nM) mGlu5PAM | Eff. (%) |
|---|---|---|---|---|
| 32 | 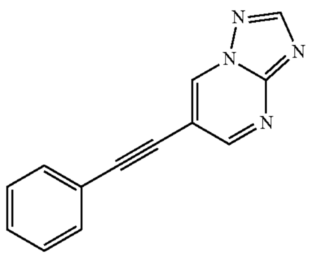 [SMILES: C(#Cc1cnc2ncnn2c1)c1ccccc1] | 6-Phenylethynyl-[1,2,4]triazolo[1,5-a]pyrimidine | 210 | 100 |
| 33 | 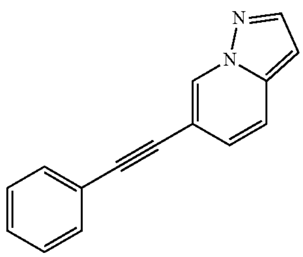 [SMILES: C(#Cc1ccc2ccnn2c1)c1ccccc1] | 6-Phenylethynyl-pyrazolo[1,5-a]pyridine | 136 | 88 |
| 34 | 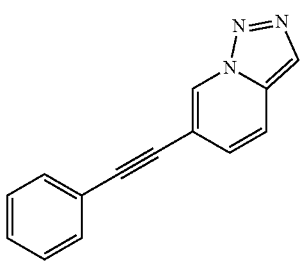 [SMILES: C(#Cc1ccc2cnnn2c1)c1ccccc1] | 6-Phenylethynyl-[1,2,3]triazolo[1,5-a]pyridine | 50 | 77 |
| 35 | 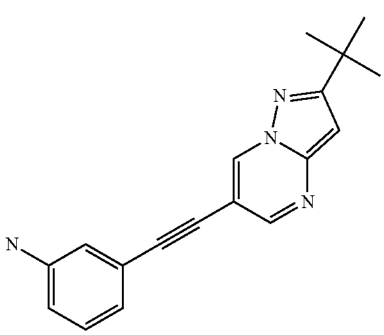 [SMILES: CC(C)(C)c1cc2ncc(C#Cc3cccc(N)c3)cn2n1] | 3-(2-tert-Butyl-pyrazolo[1,5-a]pyrimidin-6-ylethynyl)-phenylamine | 37 | 69 |
| 36 | 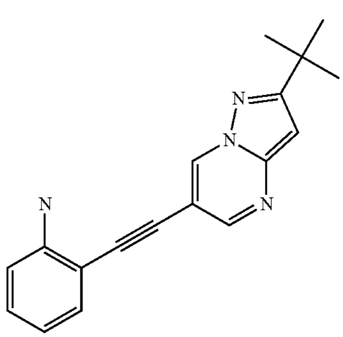 [SMILES: CC(C)(C)c1cc2ncc(C#Cc3ccccc3N)cn2n1] | 2-(2-tert-Butyl-pyrazolo[1,5-a]pyrimidin-6-ylethynyl)-phenylamine | 155 | 88 |

-continued

| Ex. | Structure | Name | EC₅₀ (nM) mGlu5PAM | Eff. (%) |
|---|---|---|---|---|
| 37 | 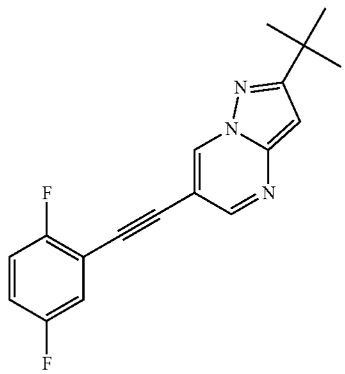 [SMILES: CC(C)(C)c1cc2ncc(C#Cc3cc(F)ccc3F)cn2n1] | 2-tert-Butyl-6-(2,5-difluoro-phenylethynyl)-pyrazolo[1,5-a]pyrimidine | 39 | 65 |
| 38 | 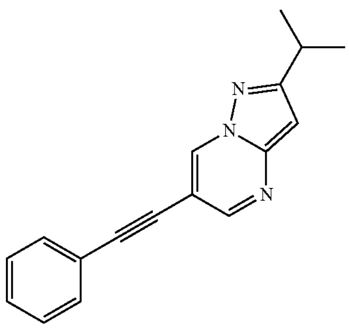 [SMILES: CC(C)c1cc2ncc(C#Cc3ccccc3)cn2n1] | 2-Isopropyl-6-phenylethynyl-pyrazolo[1,5-a]pyrimidine | 18 | 53 |
| 39 | 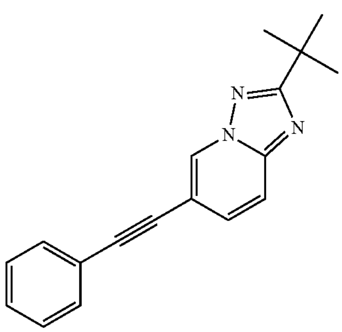 [SMILES: CC(C)(C)c1nc2ccc(C#Cc3ccccc3)cn2n1] | 2-tert-Butyl-6-phenylethynyl-[1,2,4]triazolo[1,5-a]pyridine | 30 | 54 |
| 40 | 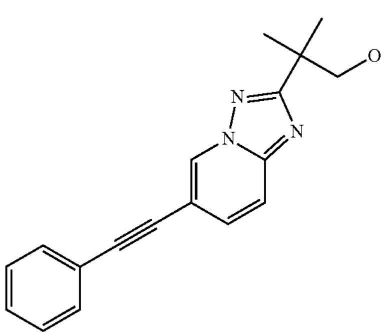 [SMILES: CC(C)(CO)c1nc2ccc(C#Cc3ccccc3)cn2n1] | 2-Methyl-2-(6-phenylethynyl-[1,2,4]triazolo[1,5-a]pyridin-2-yl)-propan-1-ol | 66 | 88 |

-continued

| Ex. | Structure | Name | EC$_{50}$ (nM) mGlu5PAM | Eff. (%) |
|---|---|---|---|---|
| 41 | 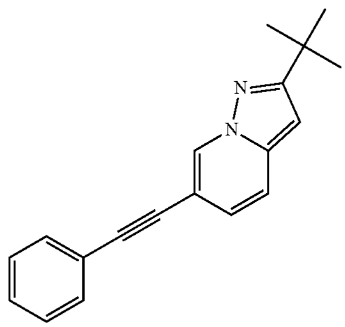 [SMILES: CC(C)(C)c1cc2ccc(C#Cc3ccccc3)cn2n1] | 2-tert-Butyl-6-phenylethynyl-pyrazolo[1,5-a]pyridine | 32 | 122 |
| 42 | 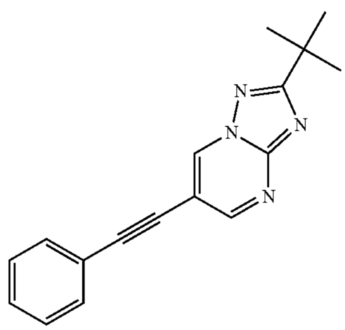 [SMILES: CC(C)(C)c1nc2ncc(C#Cc3ccccc3)cn2n1] | 2-tert-Butyl-6-phenylethynyl-[1,2,4]triazolo[1,5-a]pyrimidine | 9 | 73 |
| 43 | 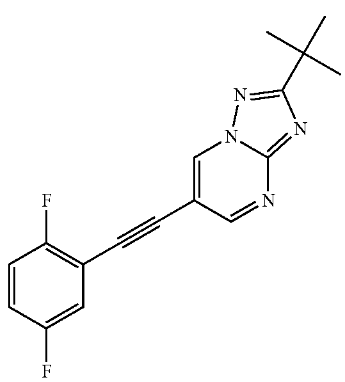 [SMILES: CC(C)(C)c1nc2ncc(C#Cc3cc(F)ccc3F)cn2n1] | 2-tert-Butyl-6-(2,5-difluoro-phenylethynyl)-[1,2,4]triazolo[1,5-a]pyrimidine | 14 | 37 |
| 44 | 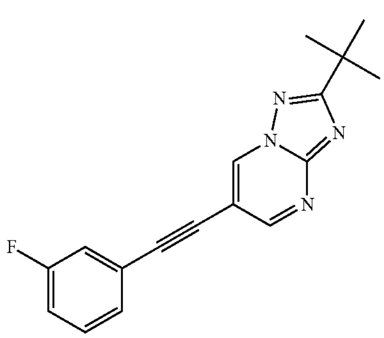 | 2-tert-Butyl-6-(3-fluoro-phenylethynyl)-[1,2,4]triazolo[1,5-a]pyrimidine | 9 | 85 |

-continued
| Ex. | Structure | Name | EC$_{50}$ (nM) mGlu5PAM | Eff. (%) |
|---|---|---|---|---|
| 45 | 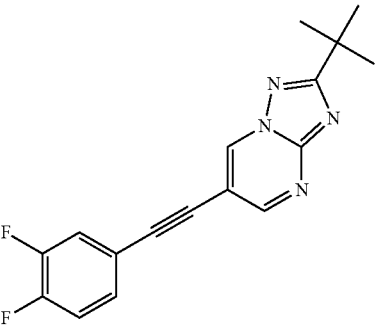 | 2-tert-Butyl-6-(3,4-difluorophenylethynyl)-[1,2,4]triazolo[1,5-a]pyrimidine | 28 | 54 |
| 46 | 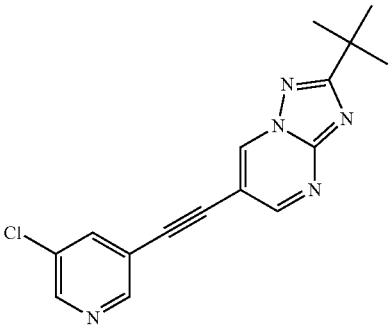 [SMILES: CC(C)(C)c1nc2ncc(C#Cc3cncc(Cl)c3)cn2n1] | 2-tert-Butyl-6-(5-chloropyridin-3-ylethynyl)-[1,2,4]triazolo[1,5-a]pyrimidine | 47 | 49 |
| 47 | 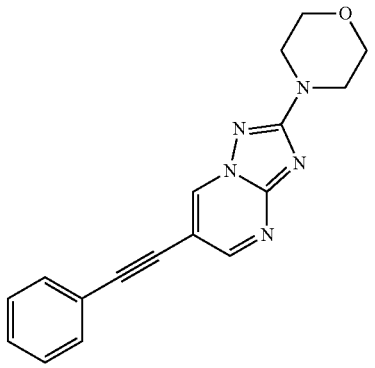 [SMILES: C(#Cc1cnc2nc(N3CCOCC3)nn2c1)c1ccccc1] | 2-Morpholin-4-yl-6-phenylethynyl-[1,2,4]triazolo[1,5-a]pyrimidine | 69 | 119 |
| 48 | 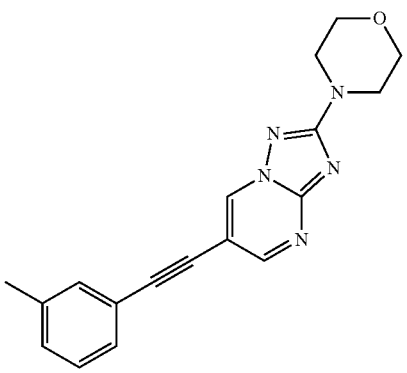 [SMILES: Cc1cccc(C#Cc2cnc3nc(N4CCOCC4)nn3c2)c1] | 2-Morpholin-4-yl-6-m-tolylethynyl-[1,2,4]triazolo[1,5-a]pyrimidine | 58 | 84 |

-continued

| Ex. | Structure | Name | EC$_{50}$ (nM) mGlu5PAM | Eff. (%) |
|---|---|---|---|---|
| 49 | 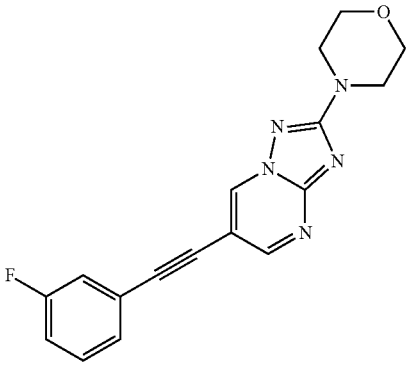 | 6-(3-Fluoro-phenylethynyl)-2-morpholin-4-yl-[1,2,4]triazolo[1,5-a]pyrimidine | 50 | 101 |
| 50 | 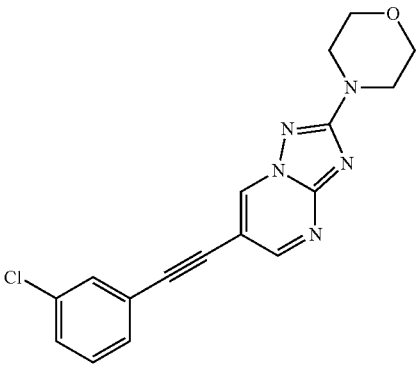 [SMILES: Clc1cccc(C#Cc2cnc3nc(N4CCOCC4)nn3c2)c1] | 6-(3-Chloro-phenylethynyl)-2-morpholin-4-yl-[1,2,4]triazolo[1,5-a]pyrimidine | 39 | 88 |
| 51 | 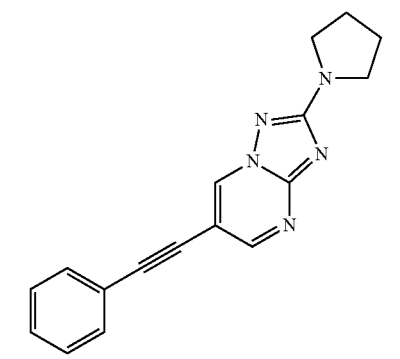 [SMILES: C(#Cc1cnc2nc(N3CCCC3)nn2c1)c1ccccc1] | 6-Phenylethynyl-2-pyrrolidin-1-yl-[1,2,4]triazolo[1,5-a]pyrimidine | 56 | 141 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

As further mentioned earlier, the use of the compounds of formula (I) for the preparation of medicaments useful in the prevention and/or the treatment of the above recited diseases is also an object of the present invention.

The dosage at which compounds of the present invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention:

Tablets of the following composition are produced in a conventional manner:

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXPERIMENTAL SECTION

Example 1

6-Phenylethynyl-pyrazolo[1,5-a]pyrimidine

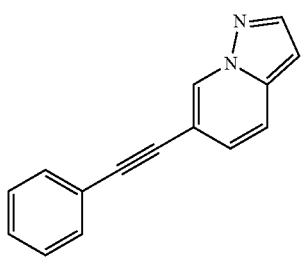 [SMILES: C(#Cc1ccc2ccnn2c1)c1ccccc1]

Bis-(triphenylphosphine)-palladium(II)dichloride (27 mg, 0.04 mmol) was dissolved in 1 ml of THF. 6-Bromo-pyrazolo [1,5-a]pyrimidine (150 mg, 0.76 mmol) and phenylacetylene (130 µl, 1.21 mmol) were added at room temperature. Triethylamine (310 µl, 2.3 mmol), triphenylphosphine (6 mg, 0.023 mmol) and copper(I) iodide (4 mg, 0.023 mmol) were added and the mixture was stirred for 2 hours at 65° C. The reaction mixture was cooled and extracted with saturated NaHCO$_3$ solution and two times with a small volume of dichloromethane. The crude product was purified by flash chromatography by directly loading the dichloromethane layers onto a silica gel column and eluting with heptane:ethyl acetate 100:0→50:50. The desired compound was obtained as a yellow solid (150 mg, 90% yield), MS: m/e=220.3 (M+H$^+$).

Example 2

2-Methyl-6-phenylethynyl-pyrazolo[1,5-a]pyrimidine

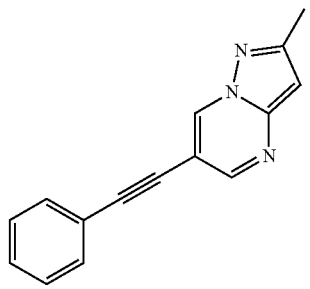 [SMILES: Cc1cc2ncc(C#Cc3ccccc3)cn2n1]

The title compound, white solid, MS: m/e=234.1 (M+H$^+$), can be prepared in accordance with the general method of example 1 from 6-bromo-2-methylpyrazolo[1,5-a]pyrimidine and phenylacetylene.

Example 3

6-(2-Fluoro-phenylethynyl)-2-methyl-pyrazolo[1,5-a]pyrimidine

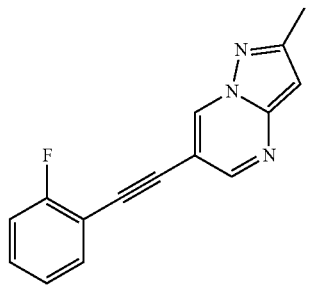 [SMILES: Cc1cc2ncc(C#Cc3ccccc3F)cn2n1]

The title compound, light yellow solid, MS: m/e=252.1 (M+H$^+$), can be prepared in accordance with the general method of example 1 from 6-bromo-2-methylpyrazolo[1,5-a]pyrimidine and 1-ethynyl-2-fluoro-benzene.

Example 4

6-(3-Fluoro-phenylethynyl)-2-methyl-pyrazolo[1,5-a]pyrimidine

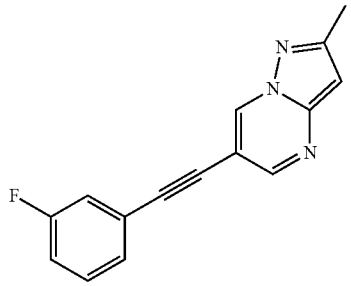 [SMILES: Cc1cc2ncc(C#Cc3cccc(F)c3)cn2n1]

The title compound, light yellow solid, MS: m/e=252.2 (M++H$^+$), can be prepared in accordance with the general method of example 1 from 6-bromo-2-methylpyrazolo[1,5-a]pyrimidine and 1-ethynyl-3-fluoro-benzene.

Example 5

6-(4-Fluoro-phenylethynyl)-2-methyl-pyrazolo[1,5-a]pyrimidine

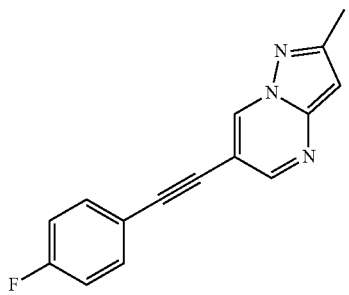 [SMILES: Cc1cc2ncc(C#Cc3ccc(F)cc3)cn2n1]

The title compound, light yellow solid, MS: m/e=252.1 (M++H+), can be prepared in accordance with the general method of example 1 from 6-bromo-2-methylpyrazolo[1,5-a]pyrimidine and 1-ethynyl-4-fluoro-benzene.

Example 6

2-Methyl-6-pyridin-4-ylethynyl-pyrazolo[1,5-a]pyrimidine

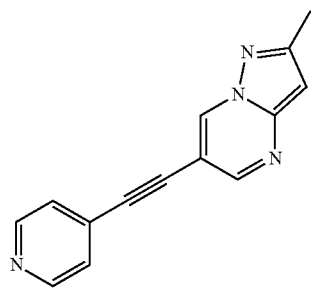 [SMILES: Cc1cc2ncc(C#Cc3ccncc3)cn2n1]

The title compound, light brown solid, MS: m/e=235.1 (M+H+), can be prepared in accordance with the general method of example 1 from 6-bromo-2-methylpyrazolo[1,5-a]pyrimidine and 4-ethynylpyridine.

Example 7

2-Methyl-6-p-tolylethynyl-pyrazolo[1,5-a]pyrimidine

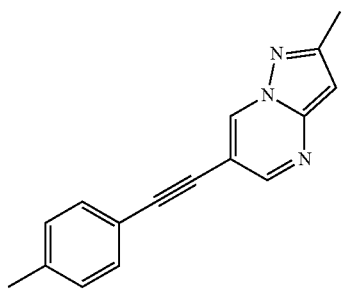

The title compound, brown solid, MS: m/e=248.2 (M+H+), can be prepared in accordance with the general method of example 1 from 6-bromo-2-methylpyrazolo[1,5-a]pyrimidine and 4-ethynyltoluene.

Example 8

6-(4-Chloro-phenylethynyl)-2-methyl-pyrazolo[1,5-a]pyrimidine

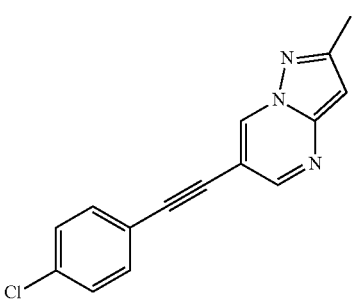 [SMILES: Cc1cc2ncc(C#Cc3ccc(Cl)cc3)cn2n1]

The title compound, brown solid, MS: m/e=268.1 (M+H+), can be prepared in accordance with the general method of example 1 from 6-bromo-2-methylpyrazolo[1,5-a]pyrimidine and 1-chloro-4-ethynylbenzene.

Example 9

2-tert-Butyl-6-phenylethynyl-pyrazolo[1,5-a]pyrimidine

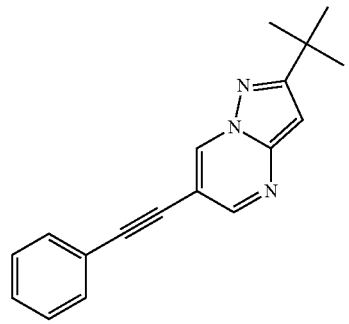 [SMILES: CC(C)(C)c1cc2ncc(C#Cc3ccccc3)cn2n1]

Step 1:
6-Bromo-2-tert-butyl-pyrazolo[1,5-a]pyrimidine

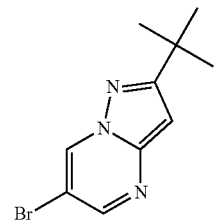

3-tert-Butyl-1H-pyrazol-5-amine (9 g, 64.7 mmol) was dissolved in BuOH (100 ml). 2-Bromomalonaldehyde (9.76 g, 64.7 mmol) and p-TsOH*H2O (615 mg, 3.23 mmol) were added at room temperature. The mixture was stirred for 16 hours at 100° C. The reaction mixture was evaporated to dryness and the residue was purified by flash chromatography on silica gel (120 gr, 0% to 40% EtOAc in heptane) and crystallization with a small volume of diisopropylether. The crystals were washed with diisopropylether and dried for 1 hour at 50° C. and <20 mbar. The desired compound was obtained as a light yellow solid (9.5 g, 58% yield), MS: m/e=256.1/254.1 (M+H$^+$).

Step 2: 2-tert-Butyl-6-phenylethynyl-pyrazolo[1,5-a]pyrimidine

The title compound, light yellow solid, MS: m/e=276.2 (M+H$^+$), can be prepared in accordance with the general method of example 1 from 6-bromo-2-tert-butyl-pyrazolo[1,5-a]pyrimidine (example 9, step 1) and phenylacetylene.

Example 10

2-tert-Butyl-6-(2-fluoro-phenylethynyl)-pyrazolo[1,5-a]pyrimidine

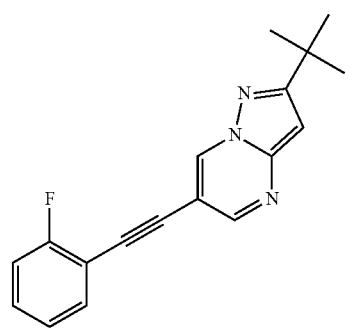

The title compound, light yellow solid, MS: m/e=294.2 (M+H$^+$), can be prepared in accordance with the general method of example 1 from 6-bromo-2-tert-butyl-pyrazolo[1,5-a]pyrimidine (example 9, step 1) and 1-ethynyl-2-fluoro-benzene.

Example 11

2-tert-Butyl-6-(3-fluoro-phenylethynyl)-pyrazolo[1,5-a]pyrimidine

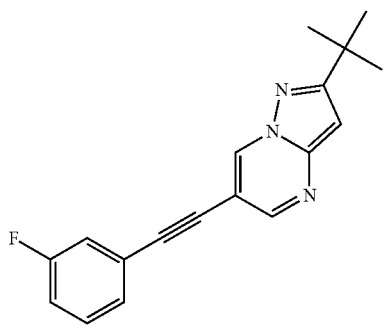 [SMILES: CC(C)(C)c1cc2ncc(C#Cc3cccc(F)c3)cn2n1]

The title compound, light yellow solid, MS: m/e=294.2 (M+H$^+$), can be prepared in accordance with the general method of example 1 from 6-bromo-2-tert-butyl-pyrazolo[1,5-a]pyrimidine (example 9, step 1) and 1-ethynyl-3-fluoro-benzene.

Example 12

2-tert-Butyl-6-(4-fluoro-phenylethynyl)-pyrazolo[1,5-a]pyrimidine

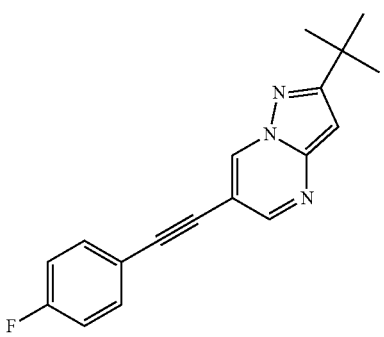 [SMILES: CC(C)(C)c1cc2ncc(C#Cc3ccc(F)cc3)cn2n1]

The title compound, light yellow solid, MS: m/e=294.2 (M+H$^+$), can be prepared in accordance with the general method of example 1 from 6-bromo-2-tert-butyl-pyrazolo[1,5-a]pyrimidine (example 9, step 1) and 1-ethynyl-4-fluoro-benzene.

Example 13

2-tert-Butyl-6-pyridin-3-ylethynyl-pyrazolo[1,5-a]pyrimidine

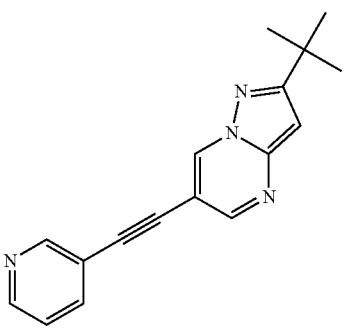 [SMILES: CC(C)(C)c1cc2ncc(C#Cc3cccnc3)cn2n1]

The title compound, white solid, MS: m/e=277.2 (M+H$^+$), can be prepared in accordance with the general method of example 1 from 6-bromo-2-tert-butyl-pyrazolo[1,5-a]pyrimidine (example 9, step 1) and 3-ethynylpyridine.

Example 14

2-tert-Butyl-6-pyridin-4-ylethynyl-pyrazolo[1,5-a]pyrimidine

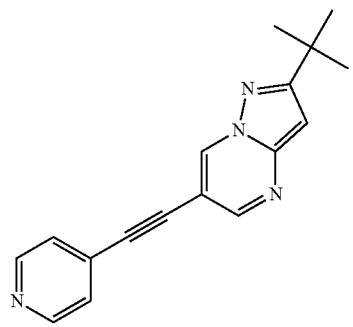

The title compound, white solid, MS: m/e=277.1 (M+H+), can be prepared in accordance with the general method of example 1 from 6-bromo-2-tert-butyl-pyrazolo[1,5-a]pyrimidine (example 9, step 1) and 4-ethynylpyridine.

Example 15

2-tert-Butyl-6-(4-methoxy-phenylethynyl)-pyrazolo[1,5-a]pyrimidine

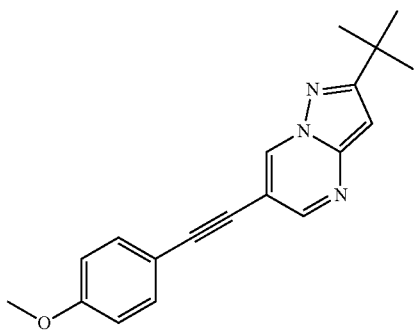 [SMILES: COc1ccc(C#Cc2cnc3cc(C(C)(C)C)nn3c2)cc1]

The title compound, yellow solid, MS: m/e=306.2 (M+H+), can be prepared in accordance with the general method of example 1 from 6-bromo-2-tert-butyl-pyrazolo[1,5-a]pyrimidine (example 9, step 1) and 1-ethynyl-4-methoxybenzene.

Example 16

2-tert-Butyl-6-m-tolylethynyl-pyrazolo[1,5-a]pyrimidine

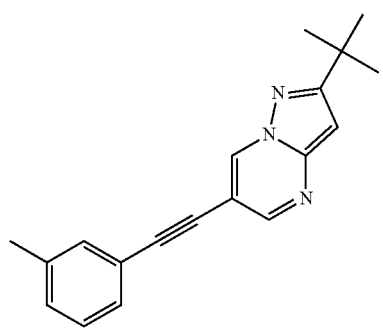 [SMILES: Cc1cccc(C#Cc2cnc3cc(C(C)(C)C)nn3c2)c1]

The title compound, yellow solid, MS: m/e=290.2 (M+H+), can be prepared in accordance with the general method of example 1 from 6-bromo-2-tert-butyl-pyrazolo[1,5-a]pyrimidine (example 9, step 1) and 1-ethynyl-3-methylbenzene.

Example 17

2-tert-Butyl-6-(3-methoxy-phenylethynyl)-pyrazolo[1,5-a]pyrimidine

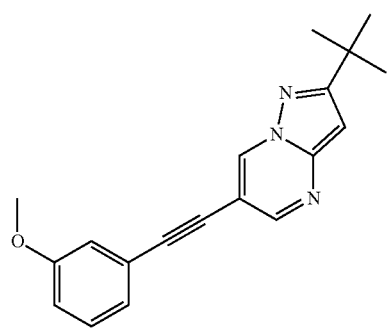

The title compound, yellow solid, MS: m/e=306.2 (M+H+), can be prepared in accordance with the general method of example 1 from 6-bromo-2-tert-butyl-pyrazolo[1,5-a]pyrimidine (example 9, step 1) and 1-ethynyl-3-methoxybenzene.

Example 18

2-Cyclobutyl-6-phenylethynyl-pyrazolo[1,5-a]pyrimidine

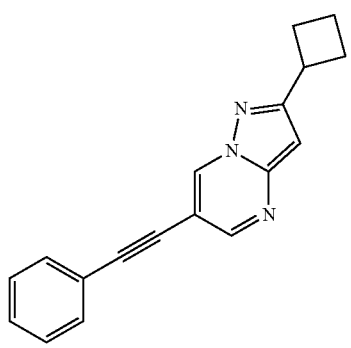 [SMILES: C(#Cc1cnc2cc(C3CCC3)nn2c1)c1ccccc1]

Step 1:
6-Bromo-2-cyclobutyl-pyrazolo[1,5-a]pyrimidine

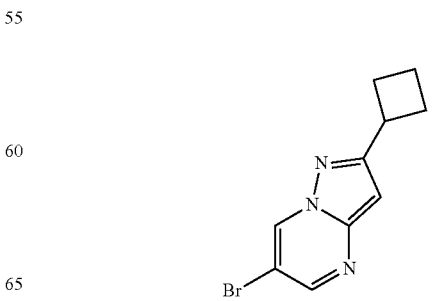

The title compound, yellow solid, MS: m/e=254.0/252.1 (M+H⁺), can be prepared in accordance with the general method of example 9, step 1 from 5-cyclobutyl-1H-pyrazol-3-ylamine and 2-bromomalonaldehyde.

Step 2: 2-Cyclobutyl-6-phenylethynyl-pyrazolo[1,5-a]pyrimidine

The title compound, light brown solid, MS: m/e=274.3 (M+H⁺), can be prepared in accordance with the general method of example 1 from 6-bromo-2-cyclobutyl-pyrazolo[1,5-a]pyrimidine (example 18, step 1) and phenylacetylene.

Example 19

2-tert-Butyl-6-p-tolylethynyl-pyrazolo[1,5-a]pyrimidine

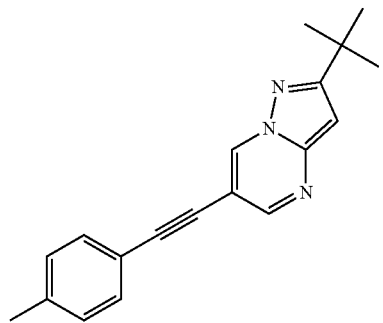 [SMILES: Cc1ccc(C#Cc2cnc3cc(C(C)(C)C)nn3c2)cc1]

The title compound, light yellow solid, MS: m/e=290.2 (M+H⁺), can be prepared in accordance with the general method of example 1 from 6-bromo-2-tert-butyl-pyrazolo[1,5-a]pyrimidine (example 9, step 1) and 1-ethynyl-4-methylbenzene.

Example 20

2-tert-Butyl-6-(4-chloro-phenylethynyl)-pyrazolo[1,5-a]pyrimidine

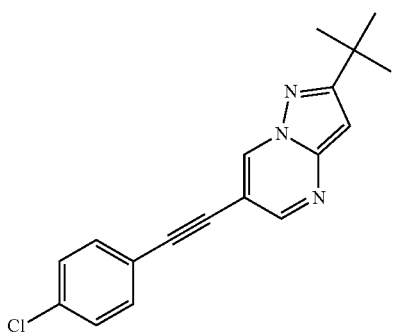

The title compound, light yellow solid, MS: m/e=310.1 (M+H⁺), can be prepared in accordance with the general method of example 1 from 6-bromo-2-tert-butyl-pyrazolo[1,5-a]pyrimidine (example 9, step 1) and 1-ethynyl-4-chlorobenzene.

Example 21

2-tert-Butyl-6-(6-chloro-pyridin-3-ylethynyl)-pyrazolo[1,5-a]pyrimidine

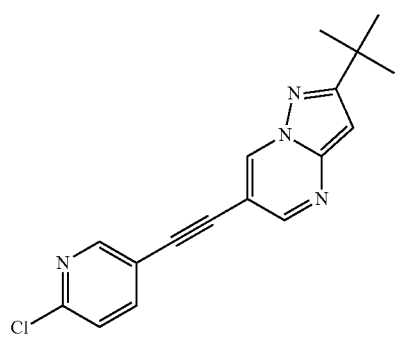 [SMILES: CC(C)(C)c1cc2ncc(C#Cc3ccc(Cl)nc3)cn2n1]

Step 1: 2-tert-Butyl-6-trimethylsilanylethynyl-pyrazolo[1,5-a]pyrimidine

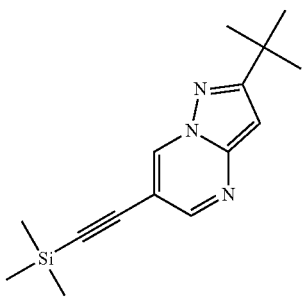 [SMILES: CC(C)(C)c1cc2ncc(C#C[Si](C)(C)C)cn2n1]

The title compound, brown solid, MS: m/e=272.3 (M++H⁺), can be prepared in accordance with the general method of example 1 from 6-bromo-2-tert-butyl-pyrazolo[1,5-a]pyrimidine (example 9, step 1) and trimethylsilylacetylene.

Step 2: 2-tert-Butyl-6-ethynyl-pyrazolo[1,5-a]pyrimidine

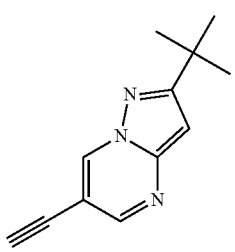

2-tert-Butyl-6-trimethylsilanylethynyl-pyrazolo[1,5-a]pyrimidine (example 21, step 1) (2.4 g, 8.85 mmol) was dissolved in dichloromethane (10 ml) and tetrabutylammoniumfluoride on silica gel (7.1 g, 10.6 mmol, 1.5 mmol/g) was added at room temperature. The mixture was stirred for 2 hours at room temperature and purified by flash chromatography by directly loading the mixture onto a 70 g silica gel column and eluting with heptane:ethyl acetate 100:0→40:60. The desired compound was obtained as a light yellow solid (1.45 g, 83% yield), MS: m/e=200.2 (M+H$^+$).

Step 3: 2-tert-Butyl-6-(6-chloro-pyridin-3-ylethynyl)-pyrazolo[1,5-a]pyrimidine

The title compound, light yellow solid, MS: m/e=311.3 (M+H$^+$), can be prepared in accordance with the general method of example 1 from 2-tert-butyl-6-ethynyl-pyrazolo[1,5-a]pyrimidine (example 21, step 2) and 2-chloro-5-iodopyridine.

Example 22

5-(2-tert-Butyl-pyrazolo[1,5-a]pyrimidin-6-ylethynyl)-pyridin-2-ylamine

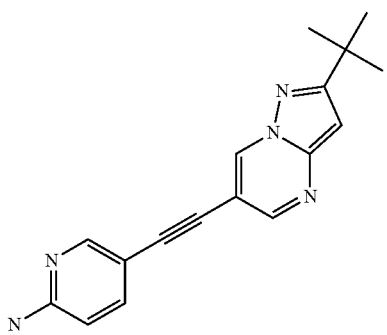

The title compound, off white solid, MS: m/e=292.1 (M+H$^+$), can be prepared in accordance with the general method of example 1 from 2-tert-butyl-6-ethynyl-pyrazolo[1,5-a]pyrimidine (example 21, step 2) and 5-iodopyridin-2-amine.

Example 23

2-tert-Butyl-6-(5-chloro-pyridin-3-ylethynyl)-pyrazolo[1,5-a]pyrimidine

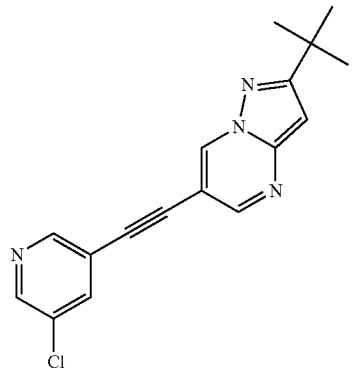

The title compound, light yellow solid, MS: m/e=311.2 (M+H$^+$), can be prepared in accordance with the general method of example 1 from 2-tert-butyl-6-ethynyl-pyrazolo[1,5-a]pyrimidine (example 21, step 2) and 3-bromo-5-chloropyridine.

Example 24

2-tert-Butyl-6-pyrimidin-5-ylethynyl-pyrazolo[1,5-a]pyrimidine

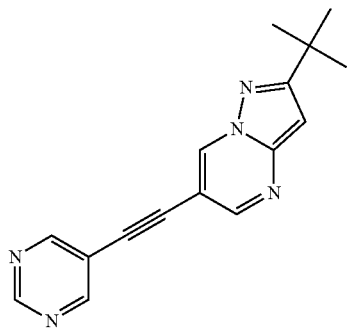 [SMILES: CC(C)(C)c1cc2ncc(C#Cc3cncnc3)cn2n1]

The title compound, light yellow solid, MS: m/e=278.2 (M+H$^+$), can be prepared in accordance with the general method of example 1 from 2-tert-butyl-6-ethynyl-pyrazolo[1,5-a]pyrimidine (example 21, step 2) and 3-bromopyrimidine.

Example 25

2-tert-Butyl-6-(3,4-difluoro-phenylethynyl)-pyrazolo[1,5-a]pyrimidine

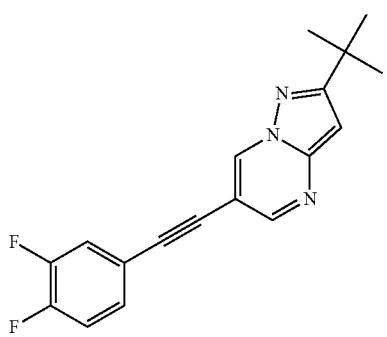 [SMILES: CC(C)(C)c1cc2ncc(C#Cc3ccc(F)c(F)c3)cn2n1]

The title compound, light yellow solid, MS: m/e=312.2 (M+H$^+$), can be prepared in accordance with the general method of example 1 from 2-tert-butyl-6-ethynyl-pyrazolo[1,5-a]pyrimidine (example 21, step 2) and 1,2-difluoro-4-iodobenzene.

Example 26

6-Phenylethynyl-2-(tetrahydro-pyran-4-yl)-pyrazolo[1,5-a]pyrimidine

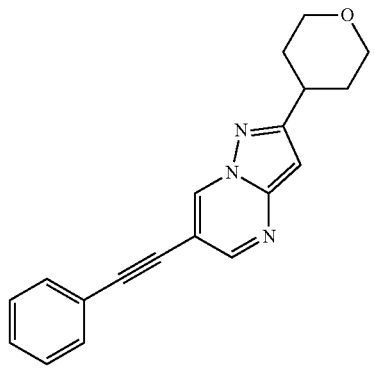

Step 1:
5-(Tetrahydro-pyran-4-yl)-2H-pyrazol-3-ylamine

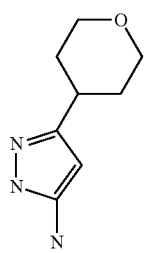 [SMILES: Nc1cc(C2CCOCC2)n[nH]1]

The title compound can be prepared in accordance with the general method described in the patent application WO2008001070 (example 114).

Step 2: 6-Bromo-2-(tetrahydro-pyran-4-yl)-pyrazolo[1,5-a]pyrimidine

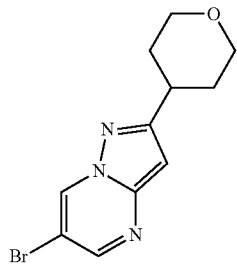 [SMILES: Brc1cnc2cc(C3CCOCC3)nn2c1]

The title compound, light brown solid, MS: m/e=284.0 (M+H$^+$), can be prepared in accordance with the general method of example 9, step 1 from 5-(tetrahydro-pyran-4-yl)-2H-pyrazol-3-ylamine (example 26, step 1) and 2-bromomalonaldehyde.

Step 3: 6-Phenylethynyl-2-(tetrahydro-pyran-4-yl)-pyrazolo[1,5-a]pyrimidine

The title compound, grey solid, MS: m/e=304.1 (M+H$^+$), can be prepared in accordance with the general method of example 1 from 6-bromo-2-(tetrahydro-pyran-4-yl)-pyrazolo[1,5-a]pyrimidine (example 26, step 2) and phenylacetylene.

Example 27

4-(2-tert-Butyl-pyrazolo[1,5-a]pyrimidin-6-ylethynyl)-phenylamine

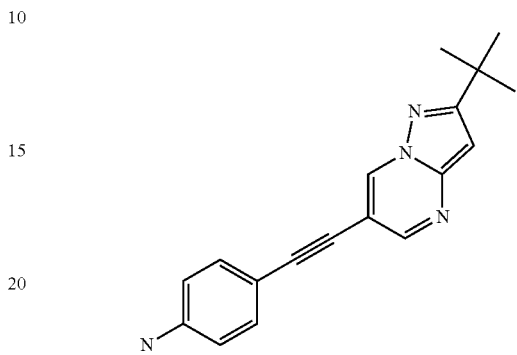

The title compound, brown solid, MS: m/e=291.2 (M+H$^+$), can be prepared in accordance with the general method of example 1 from 6-bromo-2-tert-butyl-pyrazolo[1,5-a]pyrimidine (example 9, step 1) and 4-ethynylaniline.

Example 28

2-(6-Phenylethynyl-pyrazolo[1,5-a]pyrimidin-2-yl)-propan-2-ol

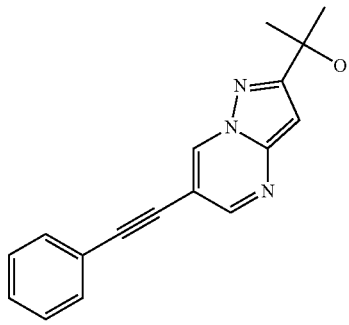 [SMILES: CC(C)(O)c1cc2ncc(C#Cc3ccccc3)cn2n1]

Step 1:
6-Bromo-pyrazolo[1,5-a]pyrimidine-2-carboxylic acid methyl ester

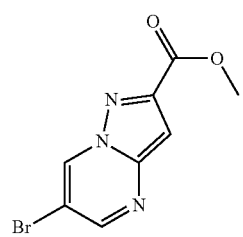

The title compound, brown solid, MS: m/e=256.0/254.1 (M+H⁺), can be prepared in accordance with the general method of example 9, step 1 from methyl 5-amino-1H-pyrazole-3-carboxylate and 2-bromomalonaldehyde.

Step 2: 6-Phenylethynyl-pyrazolo[1,5-a]pyrimidine-2-carboxylic acid methyl ester

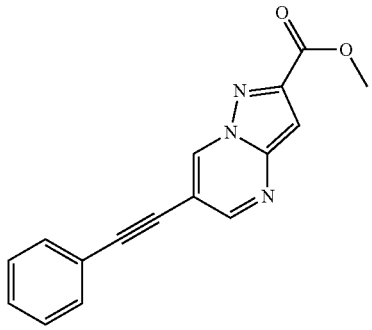 [SMILES: COC(=O)c1cc2ncc(C#Cc3ccccc3)cn2n1]

The title compound, grey solid, MS: m/e=278.2 (M+H⁺), can be prepared in accordance with the general method of example 1 from 6-bromo-pyrazolo[1,5-a]pyrimidine-2-carboxylic acid methyl ester (example 28, step 1) and phenylacetylene.

Step 3: 2-(6-Phenylethynyl-pyrazolo[1,5-a]pyrimidin-2-yl)-propan-2-ol

6-Phenylethynyl-pyrazolo[1,5-a]pyrimidine-2-carboxylic acid methyl ester (example 28, step 2) (60 mg, 0.22 mmol) was dissolved in 5 ml of THF and cooled to 0-5° C. Methylmagnesium chloride solution (150 μl, 0.45 mmol, 3N in THF) was added dropwise at 0-5° C. The reaction mixture was stirred for 30 minutes at 0-5° C. Water was added and the mixture was extracted two times with ethyl acetate. The organic extracts were dried with sodium sulfate, filtered and evaporated. The crude product was purified by flash chromatography on silica gel (heptane:EtOAc 100:0→70:30) and suspended in Et₂O. The desired compound was obtained as a light brown solid (7 mg, 12% yield), MS: m/e=278.1 (M+H⁺).

Example 29

2-tert-Butyl-6-(5-fluoro-pyridin-3-ylethynyl)-pyrazolo[1,5-a]pyrimidine

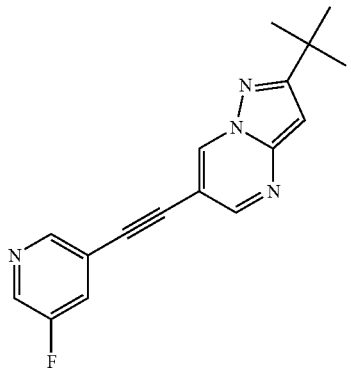 [SMILES: CC(C)(C)c1cc2ncc(C#Cc3cncc(F)c3)cn2n1]

The title compound, light yellow solid, MS: m/e=295.3 (M+H⁺), can be prepared in accordance with the general method of example 1 from 2-tert-butyl-6-ethynyl-pyrazolo[1,5-a]pyrimidine (example 21, step 2) and 3-bromo-5-fluorobenzene.

Example 30

6-Phenylethynyl-pyrazolo[1,5-a]pyrimidine-3-carbonitrile

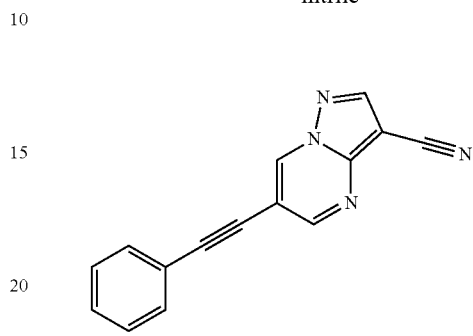

The title compound, yellow solid, MS: m/e=245.2 (M+H⁺), can be prepared in accordance with the general method of example 1 from 6-bromo-pyrazolo(1,5-A)pyrimidine-3-carbonitrile and phenylacetylene.

Example 31

6-Phenylethynyl-[1,2,4]triazolo[1,5-a]pyridine

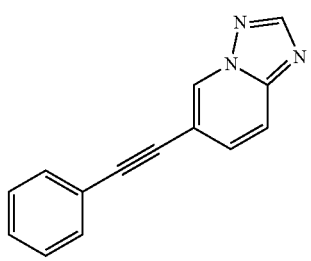 [SMILES: C(#Cc1ccc2ncnn2c1)c1ccccc1]

Step 1: 5-Phenylethynyl-pyridin-2-ylamine

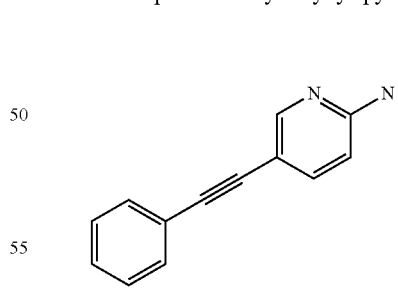

The title compound, light yellow solid, MS: m/e=195.2 (M+H⁺), can be prepared in accordance with the general method of example 1 from 2-amino-5-iodopyridine and phenylacetylene.

Step 2: 6-Phenylethynyl-[1,2,4]triazolo[1,5-a]pyridine

The title compound, white solid, MS: m/e=220.3 (M+H⁺), can be prepared in accordance with the general method described in the patent application WO2007059257 (page 109, step A, B and C) starting from 5-phenylethynyl-pyridin-2-ylamine (example 31, step 1).

Example 32

6-Phenylethynyl-[1,2,4]triazolo[1,5-a]pyrimidine

Step 1: 6-Bromo-[1,2,4]triazolo[1,5-a]pyrimidine

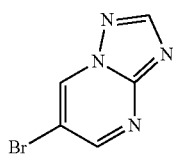

The title compound, white solid, MS: m/e=201.0/199.2 (M+H$^+$), can be prepared in accordance with the general method described in the patent application WO2007059257 (page 109, step A, B and C) starting from 2-amino-5-bromopyrimidine.

Step 2:
6-Phenylethynyl-[1,2,4]triazolo[1,5-a]pyrimidine

The title compound, light brown solid, MS: m/e=221.2 (M+H$^+$), can be prepared in accordance with the general method of example 1 from 6-bromo-[1,2,4]triazolo[1,5-a]pyrimidine (example 32, step 1) and phenylacetylene.

Example 33

6-Phenylethynyl-pyrazolo[1,5-a]pyridine

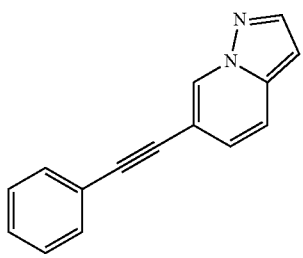 [SMILES: C(#Cc1ccc2ccnn2c1)c1ccccc1]

Step 1: Pyrazolo[1,5-a]pyridin-6-ol

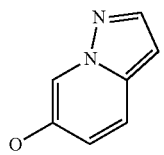

The title compound, white solid, MS: m/e=135.1 (M+H+), can be prepared in accordance with the general method described in EP1972628.

Step 2: Trifluoro-methanesulfonic acid pyrazolo[1,5-a]pyridin-6-yl ester

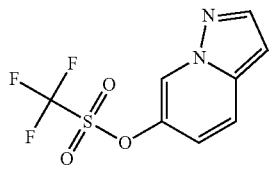 [SMILES: O=S(=O)(Oc1ccc2ccnn2c1)C(F)(F)F]

Pyrazolo[1,5-a]pyridin-6-ol (example 22, step 1) (200 mg, 1.49 mmol) was dissolved in dichloromethane (10 ml) and triethylamine (200 µl, 1.49 mmol) and trifluoromethanesulfonic anhydride (250 µl, 1.49 mmol) were added at 0-5° C. The mixture was stirred for 1 hour at room temperature and extracted then with saturated NaHCO$_3$ solution and two times with dichloromethane. The organic layers were extracted with brine, dried over Na$_2$SO$_4$, filtered and evaporated to dryness. The desired compound was obtained as white solid (400 mg, quantitative), MS: m/e=267.0 (M+H$^+$).

Step 3: 6-Phenylethynyl-pyrazolo[1,5-a]pyridine

The title compound, light yellow solid, MS: m/e=219.2 (M+H$^+$), can be prepared in accordance with the general method of example 1 from trifluoro-methanesulfonic acid pyrazolo[1,5-a]pyridin-6-yl ester (example 33, step 2) and phenylacetylene.

Example 34

6-Phenylethynyl-[1,2,3]triazolo[1,5-a]pyridine

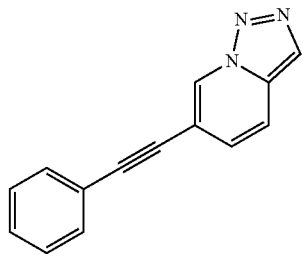 [SMILES: C(#Cc1ccc2cnnn2c1)c1ccccc1]

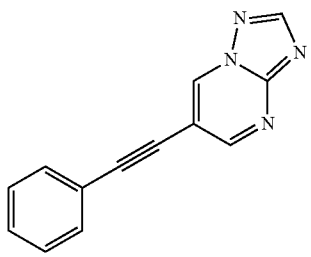

Step 1: 6-Bromo-[1,2,3]triazolo[1,5-a]pyridine

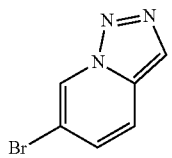

The title compound, light brown solid, MS: m/e=200.1/198.0 (M+H+), can be prepared in accordance with the general method as described in B. Abarca et al./Tetrahedron 64 (2008) 3794-3801.

Step 2: 6-Phenylethynyl-[1,2,3]triazolo[1,5-a]pyridine

The title compound, light brown solid, MS: m/e=220.3 (M+H⁺), can be prepared in accordance with the general method of example 1 from 6-bromo-[1,2,3]triazolo[1,5-a]pyridine (example 34, step 1) and phenylacetylene.

Example 35

3-(2-tert-Butyl-pyrazolo[1,5-a]pyrimidin-6-ylethynyl)-phenylamine

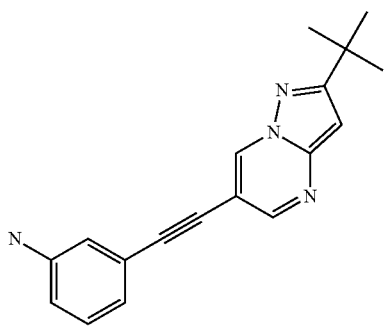 [SMILES: CC(C)(C)c1cc2ncc(C#Cc3cccc(N)c3)cn2n1]

The title compound, light yellow solid, MS: m/e=291.2 (M+H⁺), can be prepared in accordance with the general method of example 1 from 6-bromo-2-tert-butyl-pyrazolo[1,5-a]pyrimidine (example 9, step 1) and 3-ethynylaniline.

Example 36

2-(2-tert-Butyl-pyrazolo[1,5-a]pyrimidin-6-ylethynyl)-phenylamine

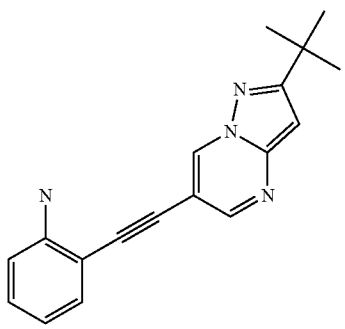 [SMILES: CC(C)(C)c1cc2ncc(C#Cc3ccccc3N)cn2n1]

The title compound, light yellow solid, MS: m/e=291.2 (M+H⁺), can be prepared in accordance with the general method of example 1 from 6-bromo-2-tert-butyl-pyrazolo[1,5-a]pyrimidine (example 9, step 1) and 2-ethynylaniline.

Example 37

2-tert-Butyl-6-(2,5-difluoro-phenylethynyl)-pyrazolo[1,5-a]pyrimidine

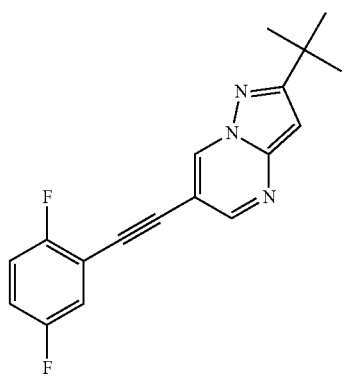 [SMILES: CC(C)(C)c1cc2ncc(C#Cc3cc(F)ccc3F)cn2n1]

The title compound, a white solid, MS: m/e=312.2 (M+H⁺), can be prepared in accordance with the general method of example 1 from 2-tert-butyl-6-ethynyl-pyrazolo[1,5-a]pyrimidine (example 21, step 2) and 1,4-difluoro-2-iodobenzene.

Example 38

2-Isopropyl-6-phenylethynyl-pyrazolo[1,5-a]pyrimidine

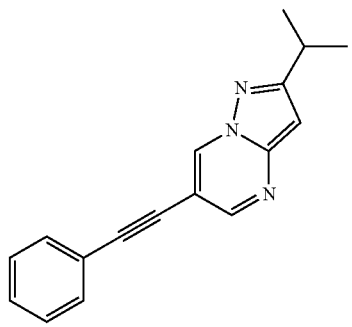 [SMILES: CC(C)c1cc2ncc(C#Cc3ccccc3)cn2n1]

Step 1: 6-Bromo-2-isopropyl-pyrazolo[1,5-a]pyrimidine

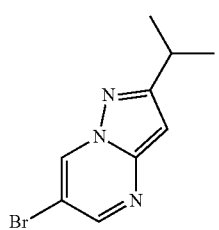

The title compound, a light yellow solid, MS: m/e=240.2/242.2 (M+H⁺), can be prepared in accordance with the general method of example 1, step 1 from 5-isopropyl-2H-pyrazol-3-ylamine.

Step 2: 2-Isopropyl-6-phenylethynyl-pyrazolo[1,5-a]pyrimidine

The title compound, a brown solid, MS: m/e=245.2 (M+H⁺), can be prepared in accordance with the general method of example 1 from 6-bromo-2-isopropyl-pyrazolo[1,5-a]pyrimidine (example 38, step 1) and phenylacetylene.

Example 39

2-tert-Butyl-6-phenylethynyl-[1,2,4]triazolo[1,5-a]pyridine

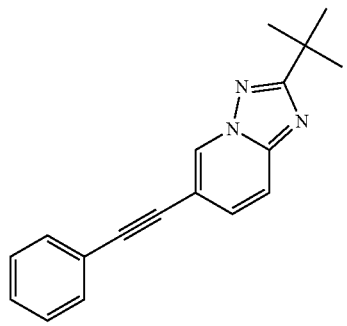 [SMILES: CC(C)(C)c1nc2ccc(C#Cc3ccccc3)cn2n1]

Step 1:
N-(5-Iodo-pyridin-2-yl)-2,2-dimethyl-propionamide

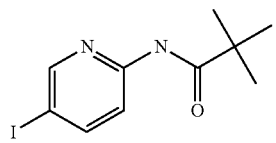

5-Iodopyridin-2-amine (5 g, 22.7 mmol) was dissolved in 50 ml of dichloromethane and Et₃N (6.3 ml, 45.5 mmol, 2 equiv.) was added at room temperature. The mixture was cooled to 0-5° C. and pivaloyl chloride (3.4 ml, 27.3 mmol, 1.2 equiv.) was added dropwise. The reaction mixture was stirred for 1 hour at 0-5° C. Saturated NaHCO₃-solution was added and the mixture was extracted with dichloromethane. The organic extracts were dried with sodium sulfate, filtered and evaporated to dryness. The desired N-(5-iodopyridin-2-yl)pivalamide (7.34 g, 99.8% yield) was obtained as a brown oil, MS: m/e=305.0 (M+H⁺).

Step 2: N-(5-Iodo-pyridin-2-yl)-2,2-dimethyl-thiopropionamide

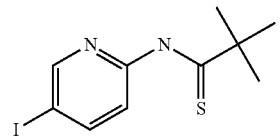

N-(5-Iodo-pyridin-2-yl)-2,2-dimethyl-propionamide (example 39, step 1) (5.8 g, 19.1 mmol) was dissolved in 30 ml of toluene and Lawesson's reagent (7.7 g, 19.1 mmol, 1 equiv.) was added at room temperature. The reaction mixture was stirred for 48 hours at 110° C. The crude product was purified by flash chromatography by directly loading the cooled toluene reaction mixture onto a 300 g silica gel column and eluting with heptane:ethyl acetate 100:0→80:20. The desired N-(5-iodo-pyridin-2-yl)-2,2-dimethyl-thiopropionamide was obtained as a yellow oil (5.1 g, 75% yield), MS: m/e=321.0 (M+H⁺).

Step 3: N-Hydroxy-N'-(5-iodo-pyridin-2-yl)-2,2-dimethyl-propionamidine

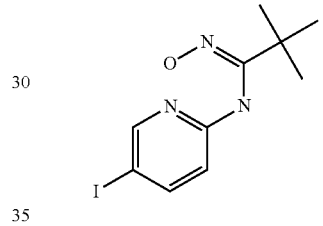

N-(5-Iodo-pyridin-2-yl)-2,2-dimethyl-thiopropionamide (example 39, step 2) (5.1 g, 15.9 mmol) was dissolved in 50 ml of EtOH and Et₃N (2.9 ml, 20.7 mmol, 1.3 equiv.) and hydroxylamine hydrochloride (1.3 g, 19.1 mmol, 1.2 equiv.) were added at room temperature. The mixture was stirred for 2 hours at room temperature. The suspension was diluted with 100 ml of water and filtered. The crystals were washed with water and dried for 2 hours at 50° C. and <10 mbar. The desired N-hydroxy-N'-(5-iodo-pyridin-2-yl)-2,2-dimethyl-propionamidine (4.35 g, 86% yield) was obtained as a white solid, MS: m/e=319.9 (M+H⁺).

Step 4:
2-tert-Butyl-6-iodo-[1,2,4]triazolo[1,5-a]pyridine

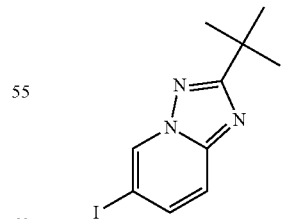

N-Hydroxy-N'-(5-iodo-pyridin-2-yl)-2,2-dimethyl-propionamidine (example 39, step 3) (2.8 g, 8.77 mmol) was suspended in 15 ml of toluene and pyridine (2.8 ml, 35.1 mmol, 4 equiv.). The mixture was cooled to 0-5° C. and p-toluenesulfonyl chloride (6.7 g, 35.1 mmol, 4 equiv.) was added. The reaction mixture was stirred for 1 hour at 0-5° C. and 4 hours at room temperature. The reaction mixture was extracted with saturated NaHCO₃ solution and two times with a small volume of dichloromethane. The crude product was purified by flash chromatography by directly loading the dichloromethane layers onto a 20 g silica gel column and eluting with heptane:ethyl acetate 100:0→0:100. The desired 2-tert-butyl-6-iodo-[1,2,4]triazolo[1,5-a]pyridine (2 g, 76% yield) was obtained as a light yellow oil, MS: m/e=302.1 (M+H⁺).

Step 5: 2-tert-Butyl-6-phenylethynyl-[1,2,4]triazolo[1,5-a]pyridine

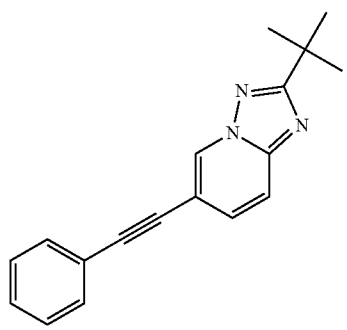 [SMILES: CC(C)(C)c1nc2ccc(C#Cc3ccccc3)cn2n1]

The title compound, a yellow solid, MS: m/e=276.2 (M+H⁺), can be prepared in accordance with the general method of example 1 from 2-tert-butyl-6-iodo-[1,2,4]triazolo[1,5-a]pyridine (example 39, step 4) and phenylacetylene.

Example 40

2-Methyl-2-(6-phenylethynyl-[1,2,4]triazolo[1,5-a]pyridin-2-yl)-propan-1-ol

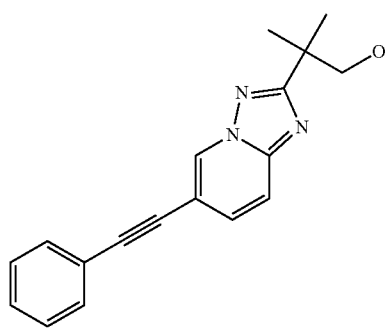 [SMILES: CC(C)(CO)c1nc2ccc(C#Cc3ccccc3)cn2n1]

Step 1: 3-Acetoxy-2,2-dimethyl-propionic acid

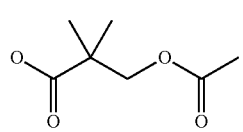

A solution of 3-hydroxy-2,2-dimethyl-propionic acid (1.5 g, 12.69 mmol) in 5 ml of acetyl chloride was heated at 80° C. under nitrogen for 2 hours. The excess of acetyl chloride was evaporated under reduced pressure. The resulting residue was dissolved in dichloromethane and washed with water. The organic layer was separated, dried and evaporated to get the desired 3-acetoxy-2,2-dimethyl-propionic acid (1.65 g, 81% yield) as a colorless liquid.

Step 2: Acetic acid 2-chlorocarbonyl-2-methyl-propyl ester

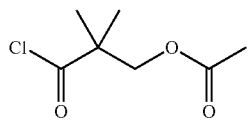

To a solution of acetoxy-2,2-dimethyl-propionic acid (example 40, step 1) (2.2 g, 13.75 mmol) in CH₂Cl₂ (25 ml), were added oxalyl chloride (2.62 ml, 27.50 mmol) and 2-4 drops of DMF and stirred at 25° C. for 3 hours. The solvent was evaporated and the resulting acetic acid 2-chlorocarbonyl-2-methyl-propyl ester (2.4 g) was used directly in next step without purification.

Step 3: Acetic acid 2-(5-iodo-pyridin-2-ylcarbamoyl)-2-methyl-propyl ester

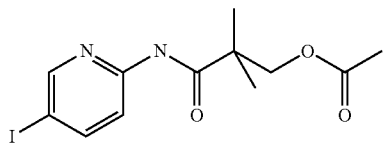 [SMILES: CC(=O)OCC(C)(C)C(=O)Nc1ccc(I)cn1]

The title compound, a white solid, MS: m/e=363.2 (M+H⁺), can be prepared in accordance with the general method of example 39, step 1 from 2-amino-5-iodopyridine and acetic acid 2-chlorocarbonyl-2-methyl-propyl ester (example 40, step 2).

Step 4: Acetic acid 2-(5-iodo-pyridin-2-ylthiocarbamoyl)-2-methyl-propyl ester

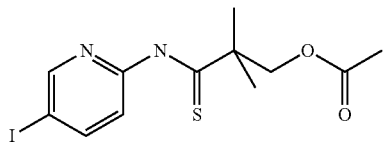 [SMILES: CC(=O)OCC(C)(C)C(=S)Nc1ccc(I)cn1]

The title compound, MS: m/e=379.4 (M+H⁺), can be prepared in accordance with the general method of example 39, step 2 from acetic acid 2-(5-iodo-pyridin-2-ylcarbamoyl)-2-methyl-propyl ester (example 40, step 3).

Step 5: Acetic acid 2-[N-hydroxy-N'-(5-iodo-pyridin-2-yl)-carbamimidoyl]-2-methyl-propyl ester

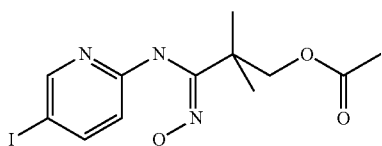 [SMILES: CC(=O)OCC(C)(C)/C(=N/O)Nc1ccc(I)cn1]

The title compound, MS: m/e=378.0 (M+H⁺), can be prepared in accordance with the general method of example 39, step 3 from acetic acid 2-(5-iodo-pyridin-2-ylthiocarbamoyl)-2-methyl-propyl ester (example 40, step 4).

Step 6: Acetic acid 2-(6-iodo-[1,2,4]triazolo[1,5-a]pyridin-2-yl)-2-methyl-propyl ester

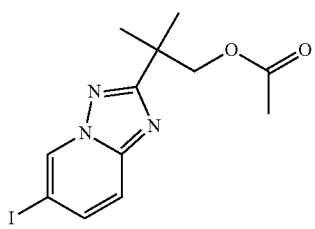 [SMILES: CC(=O)OCC(C)(C)c1nc2ccc(I)cn2n1]

The title compound, a white solid, MS: m/e=360.0 (M+H⁺), can be prepared in accordance with the general method of example 39, step 4 from acetic acid 2-[N-hydroxy-N'-(5-iodo-pyridin-2-yl)-carbamimidoyl]-2-methyl-propyl ester (example 40, step 5).

Step 7: 2-(6-Iodo-[1,2,4]triazolo[1,5-a]pyridin-2-yl)-2-methyl-propan-1-ol

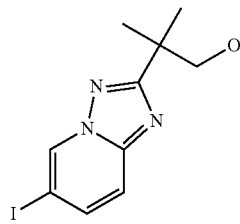

A solution of acetic acid 2-(6-iodo-[1,2,4]triazolo[1,5-a]pyridin-2-yl)-2-methyl-propyl ester (example 40, step 6) (750 mg, 2.09 mmol) and K$_2$CO$_3$ (576 mg, 4.18 mmol, 2 equiv.) in MeOH (8 ml) was stirred at 25° C. for 2 hours. The solvent was evaporated and the resulting crude product was purified by column chromatography. The desired 2-(6-iodo-[1,2,4]triazolo[1,5-a]pyridin-2-yl)-2-methyl-propan-1-ol (662 mg, 91% yield) was obtained as a white solid, MS: m/e=318.0 (M+H⁺).

Step 8: 2-Methyl-2-(6-phenylethynyl-[1,2,4]triazolo[1,5-a]pyridin-2-yl)-propan-1-ol

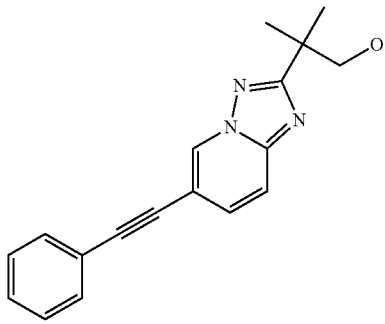 [SMILES: CC(C)(CO)c1nc2ccc(C#Cc3ccccc3)cn2n1]

The title compound, a brown solid, MS: m/e=292.0 (M+H⁺), can be prepared in accordance with the general method of example 1 from 2-(6-iodo-[1,2,4]triazolo[1,5-a]pyridin-2-yl)-2-methyl-propan-1-ol (example 40, step 7) and phenylacetylene.

Example 41

2-tert-Butyl-6-phenylethynyl-pyrazolo[1,5-a]pyridine

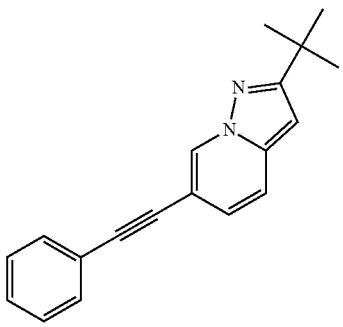 [SMILES: CC(C)(C)c1cc2ccc(C#Cc3ccccc3)cn2n1]

Step 1: 1-Amino-3-bromo-pyridinium 2,4-dinitro-phenolate

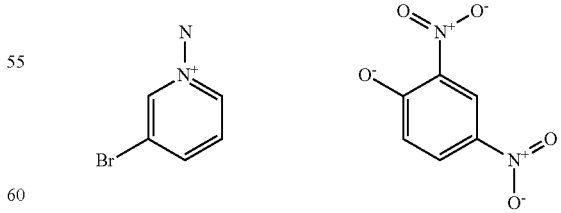

To a solution of 3-bromopyridine (2.3 g, 15.0 mmol) in acetonitrile (4 ml) was added 0-(2,4-dinitro-phenyl)-hydroxylamine (3.0 g, 15.0 mmol, 1 equiv.) and the reaction mixture was stirred at 40° C. for 16 hours. Then the solvent was evaporated, the resulting residue was triturated with ether and dried to get the desired 1-amino-3-bromo-pyridinium 2,4-dinitro-phenolate (4.5 g, 85% yield) as a brown solid.

Step 2: 6-bromo-2-tert-butyl-pyrazolo[1,5-a]pyridine-3-carboxylic acid methyl ester

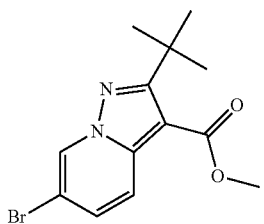 [SMILES: COC(=O)c1c(C(C)(C)C)nn2cc(Br)ccc12]

To a solution of 1-amino-3-bromo-pyridinium 2,4-dinitro-phenolate (example 41, step 1) (1.98 g, 14.16 mmol) in DMF (20 ml) were added 4,4-dimethyl-pent-2-ynoic acid methyl ester (CAS 20607-85-6) (5 g, 14.16 mmol, 1 equiv.) and $K_2CO_3$ (3.9 g, 28.3 mmol, 2 equiv.) and stirred at 25° C. while purging air. DMF was completely evaporated, the residue dissolved in ethyl acetate and washed with water (100 ml). The organic extract was dried with sodium sulfate, filtered and evaporated to dryness. The resulting crude product along with the undesired regioisomer 4-bromo-2-tert-butyl-pyrazolo[1,5-a]pyridine-3-carboxylic acid methyl ester was purified by column chromatography. The desired 6-bromo-2-tert-butyl-pyrazolo[1,5-a]pyridine-3-carboxylic acid methyl ester (1.04 g, 24% yield) was obtained as a white solid, MS: m/e=312.2 (M+H$^+$).

Step 3: 6-Bromo-2-tert-butyl-pyrazolo[1,5-a]pyridine

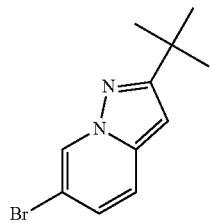

A solution of 6-bromo-2-tert-butyl-pyrazolo[1,5-a]pyridine-3-carboxylic acid methyl ester (example 41, step 2) (1.1 g, 3.53 mmol) in $H_2SO_4$ (5 ml) and $H_2O$ (5 ml) was heated at 80° C. for 36 hours. The reaction mixture was neutralized with 2N sodium hydroxide and extracted with ethyl acetate (4×60 ml). The organic extracts were dried with sodium sulfate, filtered and evaporated to dryness. The crude product was purified by flash chromatography on silica gel (heptane:EtOAc 95:5→90:10). The desired 6-bromo-2-tert-butyl-pyrazolo[1,5-a]pyridine (370 mg, 38% yield) was obtained as a white solid, MS: m/e=254.2 (M+H$^+$).

Step 4: 2-tert-Butyl-6-phenylethynyl-pyrazolo[1,5-a]pyridine

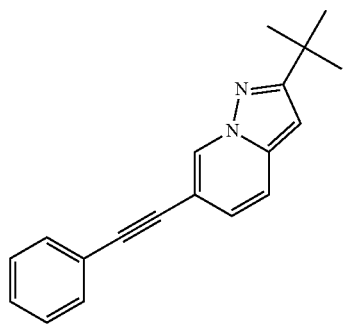 [SMILES: CC(C)(C)c1cc2ccc(C#Cc3ccccc3)cn2n1]

The title compound, a white solid, MS: m/e=275.4 (M+H$^+$), can be prepared in accordance with the general method of example 1 from 6-bromo-2-tert-butyl-pyrazolo[1,5-a]pyridine (example 41, step 3) and phenylacetylene.

Example 42

2-tert-Butyl-6-phenylethynyl-[1,2,4]triazolo[1,5-a]pyrimidine

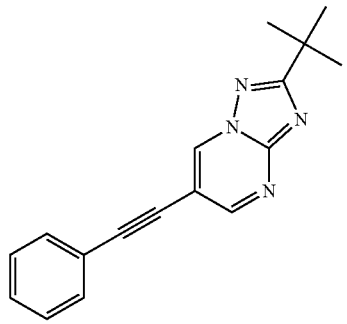 [SMILES: CC(C)(C)c1nc2ncc(C#Cc3ccccc3)cn2n1]

Step 1: 6-Bromo-2-tert-butyl-[1,2,4]triazolo[1,5-a]pyrimidine

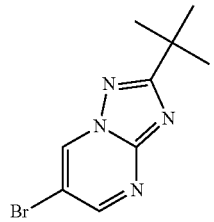

3-tert-Butyl-1H-1,2,4-triazol-5-amine (CAS 202403-45-0) (35%, 13 g, 32.5 mmol) was dissolved in acetic acid (50 ml) and 2-bromomalonaldehyde (7.35 g, 48.7 mmol, 1.5 equiv.) was added. The reaction mixture was stirred for 3 hours at 60° C. The reaction mixture was evaporated and neutralized with saturated $NaHCO_3$ solution 2N and extracted two times with dichloromethane. The organic extracts were dried with sodium sulfate, filtered and evaporated to dryness. The crude product was purified by flash chromatography on 70 g silica gel (heptane:EtOAc 100:0→50:50). The desired 6-bromo-2-tert-butyl-[1,2,4]triazolo[1,5-a]pyrimidine (6.83 g, 83% yield) was obtained as a white solid, MS: m/e=255.0/257.1 (M+H$^+$).

Step 2: 2-tert-Butyl-6-phenylethynyl-[1,2,4]triazolo[1,5-a]pyrimidine

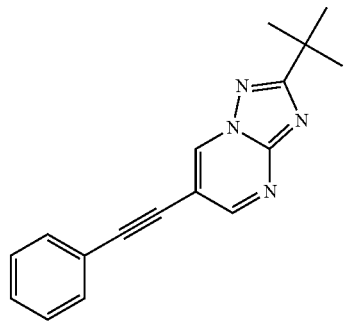 [SMILES: CC(C)(C)c1nc2ncc(C#Cc3ccccc3)cn2n1]

The title compound, a yellow solid, MS: m/e=277.1 (M+H⁺), can be prepared in accordance with the general method of example 1 from 6-bromo-2-tert-butyl-[1,2,4]triazolo[1,5-a]pyrimidine (example 42, step 1) and phenylacetylene.

Example 43

2-tert-Butyl-6-(2,5-difluoro-phenylethynyl)-[1,2,4]triazolo[1,5-a]pyrimidine

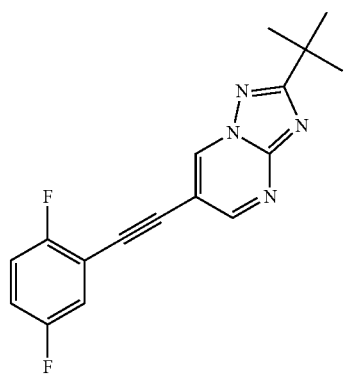 [SMILES: CC(C)(C)c1nc2ncc(C#Cc3cc(F)ccc3F)cn2n1]

Step 1: 2-tert-Butyl-6-trimethylsilanylethynyl-[1,2,4]triazolo[1,5-a]pyrimidine

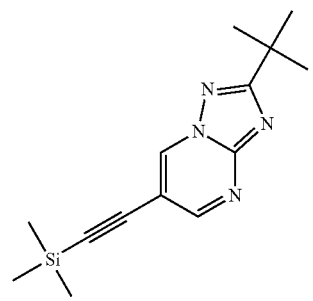 [SMILES: CC(C)(C)c1nc2ncc(C#C[Si](C)(C)C)cn2n1]

The title compound, a light yellow solid, MS: m/e=273.3 (M+H⁺), can be prepared in accordance with the general method of example 1 from 6-bromo-2-tert-butyl-[1,2,4]triazolo[1,5-a]pyrimidine (example 42, step 1) and ethynyl-trimethyl-silane.

Step 2: 2-tert-Butyl-6-(2,5-difluoro-phenylethynyl)-[1,2,4]triazolo[1,5-a]pyrimidine

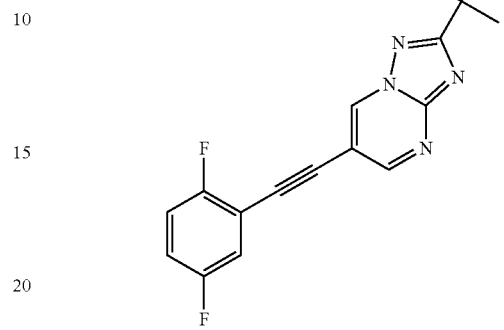

2-tert-Butyl-6-trimethylsilanylethynyl-[1,2,4]triazolo[1,5-a]pyrimidine (example 43, step 1) (100 mg, 0.37 mmol) was dissolved in DMF (1 ml). 1,4-Difluoro-2-iodobenzene (176 mg, 0.73 mmol, 2 equiv.), Et₃N (150 µl, 1.1 mmol, 3 equiv.), Bis-(triphenylphosphine)-palladium(II)dichloride (13 mg, 0.02 mmol, 0.05 equiv.), triphenylphosphine (3 mg, 0.011 mmol, 0.03 equiv.) and copper(I)iodide (2 mg, 0.011, 0.03 equiv.) were added under nitrogen and the mixture was heated to 80° C. TBAF 1M in THF (440 µl, 0.44 mmol, 1.2 equiv.) was added dropwise in 20 minutes at 80° C. The reaction mixture was stirred for 5 minutes at 80° C. The reaction mixture was evaporated and extracted with saturated NaHCO₃ solution and two times with a small volume of dichloromethane. The crude product was purified by flash chromatography by directly loading the dichloromethane layers onto a 20 g silica gel column and eluting with heptane:ethyl acetate 100:0→50:50. The desired 2-tert-butyl-6-(2,5-difluoro-phenylethynyl)-[1,2,4]triazolo[1,5-a]pyrimidine (73 mg, 64% yield) was obtained as a light yellow solid, MS: m/e=313.1 (M+H⁺).

Example 44

2-tert-Butyl-6-(3-fluoro-phenylethynyl)-[1,2,4]triazolo[1,5-a]pyrimidine

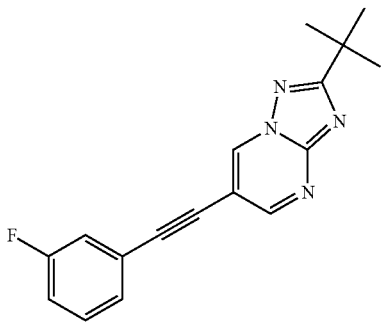

The title compound, a light yellow solid, MS: m/e=295.2 (M+H⁺), can be prepared in accordance with the general method of example 1 from 6-bromo-2-tert-butyl-[1,2,4]triazolo[1,5-a]pyrimidine (example 42, step 1) and ethynyl-3-fluorobenzene.

Example 45

2-tert-Butyl-6-(3,4-difluoro-phenylethynyl)-[1,2,4]triazolo[1,5-a]pyrimidine

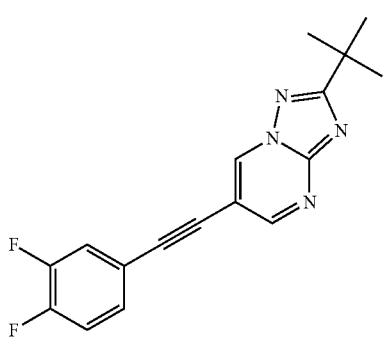 [SMILES: CC(C)(C)c1nc2ncc(C#Cc3ccc(F)c(F)c3)cn2n1]

The title compound, a light yellow solid, MS: m/e=313.1 (M+H⁺), can be prepared in accordance with the general method of example 43, step 2 from 2-tert-butyl-6-trimethyl-silanylethynyl-[1,2,4]triazolo[1,5-a]pyrimidine (example 43, step 1) and 3,4-difluoro-4-iodobenzene.

Example 46

2-tert-Butyl-6-(5-chloro-pyridin-3-ylethynyl)-[1,2,4]triazolo[1,5-a]pyrimidine

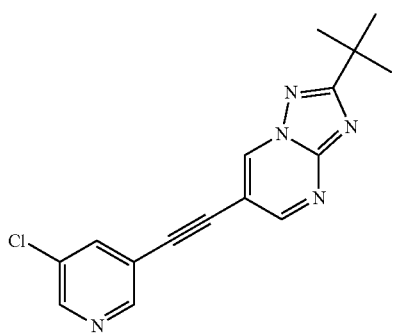 [SMILES: CC(C)(C)c1nc2ncc(C#Cc3cncc(Cl)c3)cn2n1]

The title compound, a light yellow solid, MS: m/e=312.2/314.1 (M+H⁺), can be prepared in accordance with the general method of example 43, step 2 from 2-tert-butyl-6-trimethylsilanylethynyl-[1,2,4]triazolo[1,5-a]pyrimidine (example 43, step 1) and 3-chloro-5-iodopyridine.

Example 47

2-Morpholin-4-yl-6-phenylethynyl-[1,2,4]triazolo[1,5-a]pyrimidine

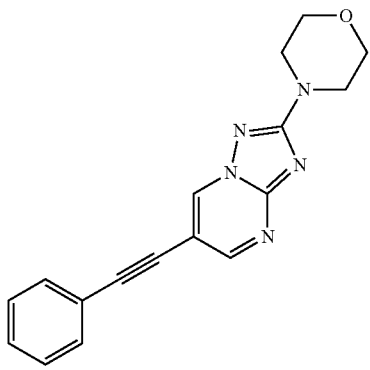 [SMILES: C(#Cc1cnc2nc(N3CCOCC3)nn2c1)c1ccccc1]

Step 1: 6-Bromo-2-morpholin-4-yl-[1,2,4]triazolo[1,5-a]pyrimidine

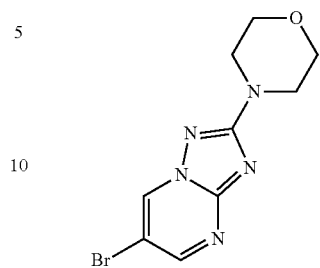

The title compound, a light yellow solid, MS: m/e=284.2/286.1 (M+H⁺), can be prepared in accordance with the general method of example 42, step 1 from 5-morpholin-4-yl-2H-[1,2,4]triazol-3-ylamine (CAS 51420-46-3) and 2-bromomalonaldehyde.

Step 2: 2-Morpholin-4-yl-6-phenylethynyl-[1,2,4]triazolo[1,5-a]pyrimidine

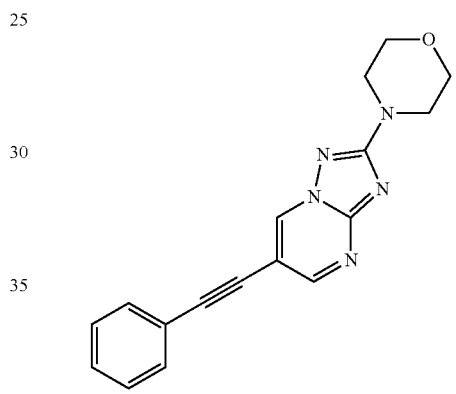

The title compound, a light brown solid, MS: m/e=306.1 (M+H⁺), can be prepared in accordance with the general method of example 1 from 6-bromo-2-morpholin-4-yl-[1,2,4]triazolo[1,5-a]pyrimidine (example 47, step 1) and phenylacetylene.

Example 48

2-Morpholin-4-yl-6-m-tolylethynyl-[1,2,4]triazolo[1,5-a]pyrimidine

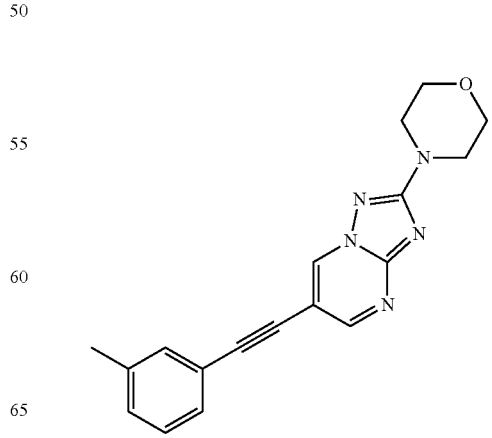

The title compound, a brown solid, MS: m/e=320.2 (M+H⁺), can be prepared in accordance with the general method of example 1 from 6-bromo-2-morpholin-4-yl-[1,2,4]triazolo[1,5-a]pyrimidine (example 47, step 1) and ethynyl-3-methylbenzene.

Example 49

6-(3-Fluoro-phenylethynyl)-2-morpholin-4-yl-[1,2,4]triazolo[1,5-a]pyrimidine

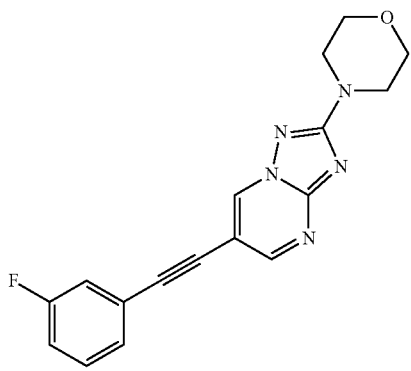 [SMILES: Fc1cccc(C#Cc2cnc3nc(N4CCOCC4)nn3c2)c1]

The title compound, a light brown solid, MS: m/e=324.3 (M+H⁺), can be prepared in accordance with the general method of example 1 from 6-bromo-2-morpholin-4-yl-[1,2,4]triazolo[1,5-a]pyrimidine (example 47, step 1) and ethynyl-3-fluorobenzene.

Example 50

6-(3-Chloro-phenylethynyl)-2-morpholin-4-yl-[1,2,4]triazolo[1,5-a]pyrimidine

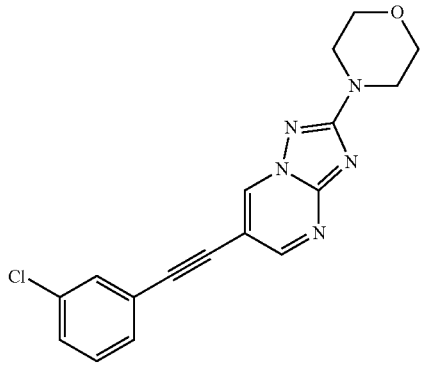 [SMILES: Clc1cccc(C#Cc2cnc3nc(N4CCOCC4)nn3c2)c1]

The title compound, a light brown solid, MS: m/e=340.0/342.1 (M+H⁺), can be prepared in accordance with the general method of example 1 from 6-bromo-2-morpholin-4-yl-[1,2,4]triazolo[1,5-a]pyrimidine (example 47, step 1) and ethynyl-3-chlorobenzene.

Example 51

6-Phenylethynyl-2-pyrrolidin-1-yl-[1,2,4]triazolo[1,5-a]pyrimidine

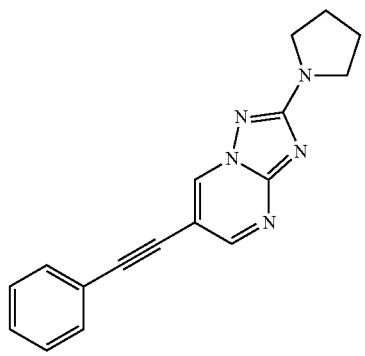 [SMILES: C(#Cc1cnc2nc(N3CCCC3)nn2c1)c1ccccc1]

Step 1: 6-Bromo-2-pyrrolidin-1-yl-[1,2,4]triazolo[1,5-a]pyrimidine

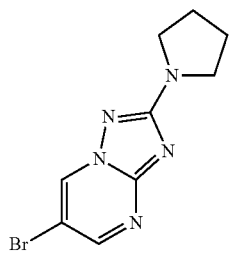 [SMILES: Brc1cnc2nc(N3CCCC3)nn2c1]

The title compound, a light red solid, MS: m/e=268.1/270.1 (M+H⁺), can be prepared in accordance with the general method of example 42, step 1 from 5-pyrrolidin-1-yl-1H-[1,2,4]triazol-3-ylamine (CAS 154956-89-5) and 2-bromomalonaldehyde.

Step 2: 6-Phenylethynyl-2-pyrrolidin-1-yl-[1,2,4]triazolo[1,5-a]pyrimidine

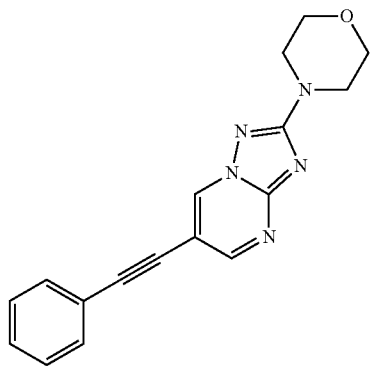 [SMILES: C(#Cc1cnc2nc(N3CCOCC3)nn2c1)c1ccccc1]

The title compound, a light brown solid, MS: m/e=290.2 (M+H⁺), can be prepared in accordance with the general method of example 1 from 6-bromo-2-pyrrolidin-1-yl-[1,2,4]triazolo[1,5-a]pyrimidine (example 51, step 1) and phenylacetylene.

The invention claimed is:

1. A compound selected from the group consisting of:
6-Phenylethynyl-[1,2,4]triazolo[1,5-a]pyridine;
2-tert-Butyl-6-phenylethynyl-[1,2,4]triazolo[1,5-a]pyridine;
2-Methyl-2-(6-phenylethynyl-[1,2,4]triazolo[1,5-a]pyridin-2-yl)-propan-1-ol;
6-Phenylethynyl-pyrazolo[1,5-a]pyridine;
2-tert-Butyl-6-phenylethynyl-pyrazolo[1,5-a]pyridine; and
6-Phenylethynyl-[1,2,3]triazolo[1,5-a]pyridine,
or a pharmaceutically acceptable salt thereof.

2. The compound of claim 1, which compound is 2-tert-Butyl-6-phenylethynyl-[1,2,4]triazolo[1,5-a]pyridine.

3. A pharmaceutical composition, comprising a therapeutically effective amount of a compound according to claim 1, or a pharmaceutically acceptable salt or acid addition salt, a racemic mixture, an enantiomer, an optical isomer or stereoisomer thereof, and a pharmaceutically acceptable carrier.

\* \* \* \* \*